(12) United States Patent
Bachmann et al.

(10) Patent No.: US 9,447,099 B2
(45) Date of Patent: Sep. 20, 2016

(54) METHODS FOR THE PREPARATION OF 5-[2-[7 (TRIFLUOROMETHYL)-5-[4-(TRIFLUOROMETHYL)PHENYL]PYRAZOLO[1,5-A]PYRIMIDIN-3-YL[ETHYNYL]-2-PYRIDINAMINE

(71) Applicant: Roche Carolina Inc., Florence, SC (US)

(72) Inventors: Stephan Bachmann, Allschwil (CH); Daniel Bailey, Buffalo, NY (US); Jodie Brice, Florence, SC (US); Miall Cedilote, Florence, SC (US); Zhiming Dong, Florence, SC (US); Stefan Hildbrand, Gelterkinden (CH); Doreen Miller, Greensboro, NC (US); Paul Spurr, Riehen (CH); Amit Srivastava, Aiken, SC (US); Juergen Wichmann, Steinen (DE); Thomas Woltering, Freiburg (DE); Jason Yang, Pleasanton, CA (US); Pingsheng Zhang, Florence, SC (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 522 days.

(21) Appl. No.: 13/628,069

(22) Filed: Sep. 27, 2012

(65) Prior Publication Data

US 2013/0085278 A1 Apr. 4, 2013

Related U.S. Application Data

(60) Provisional application No. 61/684,181, filed on Aug. 17, 2012, provisional application No. 61/542,837, filed on Oct. 4, 2011.

(51) Int. Cl.
*C07D 213/73* (2006.01)
*C07D 487/04* (2006.01)

(52) U.S. Cl.
CPC ........... *C07D 487/04* (2013.01); *C07D 213/73* (2013.01)

(58) Field of Classification Search
CPC ..................................................... C07D 213/73
USPC .......................................................... 546/311
See application file for complete search history.

(56) References Cited

U.S. PATENT DOCUMENTS 7,238,808 B2 * 7/2007 McArthur et al. ............ 544/281

FOREIGN PATENT DOCUMENTS

| WO | 2004/111040 | 12/2004 |
| WO | 2006099972 | 9/2006 |

OTHER PUBLICATIONS

<http://www.name-reaction.com/sonogashira-cross-coupling>, downloaded Aug. 13, 2015.*
(International Search Report PCT/EP2012/069303 Jan. 3, 2013).

* cited by examiner

*Primary Examiner* — Susanna Moore
(74) *Attorney, Agent, or Firm* — Tamara A. Kale

(57) ABSTRACT

The present invention provides methods for preparing 5-[2-[7-(trifluoromethyl)-5-[4-(trifluoromethyl)phenyl]pyrazolo[1,5-a]pyrimidin-3-yl]ethynyl]-2-pyridinamine (compound A), which is useful for the treatment of depression and other CNS disorders. The present methods are useful for preparing compound A on large scale in manufacturing facilities.

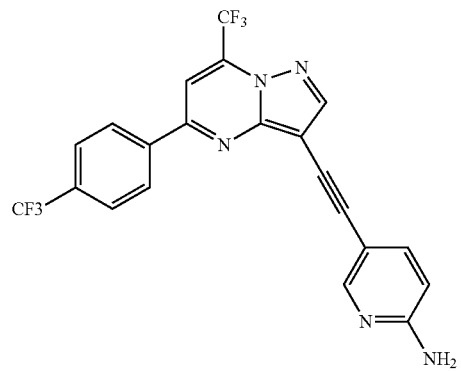

1 Claim, No Drawings

METHODS FOR THE PREPARATION OF 5-[2-[7 (TRIFLUOROMETHYL)-5-[4-(TRIFLUOROMETHYL)PHENYL]PYRAZOLO[1,5-A]PYRIMIDIN-3-YL[ETHYNYL]-2-PYRIDINAMINE

PRIORITY TO RELATED APPLICATIONS

This application claims the benefit of U.S. Provisional Application No. 61/684,181, filed Aug. 17, 2012 and U.S. Provisional Application No. 61/542,837, filed Oct. 4, 2011. The entire contents of the above-identified applications are hereby incorporated by reference.

FIELD OF THE INVENTION

The present invention provides novel methods for preparing 5-[2-[7-(trifluoromethyl)-5-[4-(trifluoromethyl)phenyl]pyrazolo[1,5-a]pyrimidin-3-yl]ethynyl]-2-pyridinamine (compound A). The present methods are useful for preparing compound A on large scale in manufacturing facilities.

BACKGROUND OF THE INVENTION

5-[2-[7-(Trifluoromethyl)-5-[4-(trifluoromethyl)phenyl]pyrazolo[1,5-a]pyrimidin-3-yl]ethynyl]-2-pyridinamine (compound A) is a mGluR2 (metabotropic glutamate receptor) antagonist, which is useful for the treatment of depression and other CNS disorders. WO 2006/099972 describes a synthesis of compound A and its potential applications in treating central nervous system (CNS) disorders. Also disclosed in WO 2006/099972 are analogues and synthetic methods for making these analogues. These methods are unsuitable for the large scale manufacture of compound A required to support clinical programs and commercialization.

SUMMARY OF THE INVENTION

The present invention provides methods for preparing compound A having the formula:

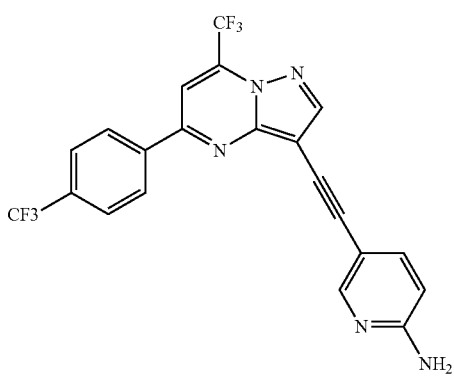

which comprise:
(a) reacting compound 3 or 7;

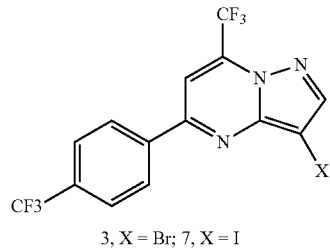

3, X = Br; 7, X = I with trimethylsilylacetylene via a Sonogashira coupling reaction in an inert solvent to provide compound 4;

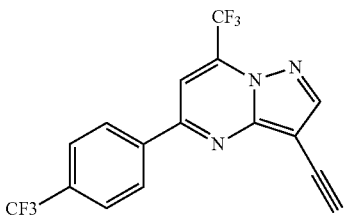

b) desilylating compound 4 in an inert solvent to provide compound 5;

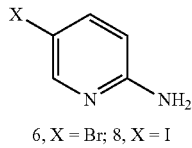

and
(c) reacting compound 5 with compound 6 or 8;

X—⟨pyridine⟩—NH₂

6, X = Br; 8, X = I via a Sonogashira coupling reaction in an inert solvent to provide compound A.

The present invention further provides methods for preparing compound A having the formula:

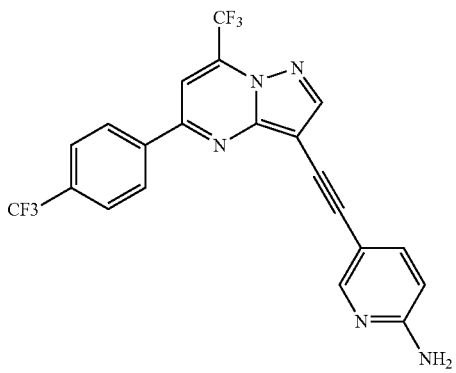

which comprise reacting compound 3 or 7;

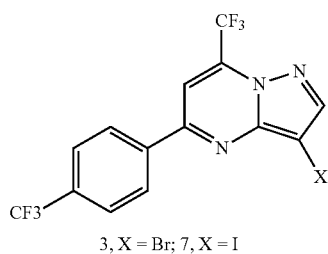

with compound 9;

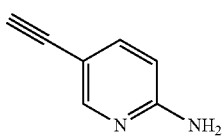

via a Sonogashira coupling reaction in an inert solvent to provide compound A.

The present invention further provides methods for preparing compound A having the formula:

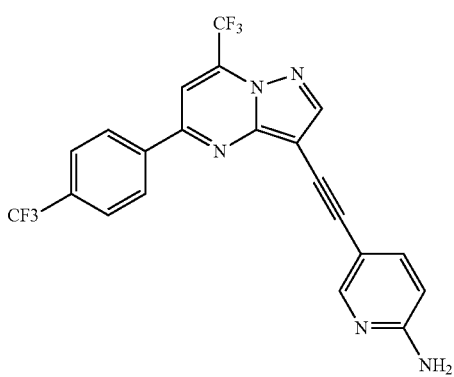

which comprise: (a) reacting compound 6 or 8;

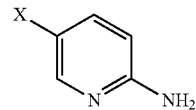

with trimethylsilylacetylene via a Sonogashira coupling reaction in an inert solvent to provide intermediate compound 12;

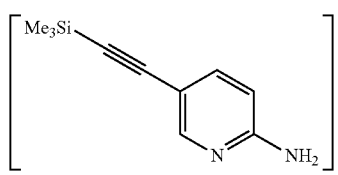

and
(b) reacting compound 12 with compound 7;

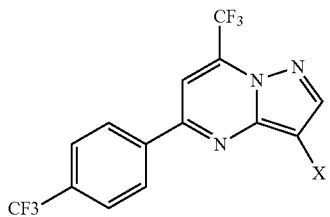

in an inert solvent in the presence of potassium fluoride to provide compound A.

The present invention further provides methods for purifying compound A having the formula:

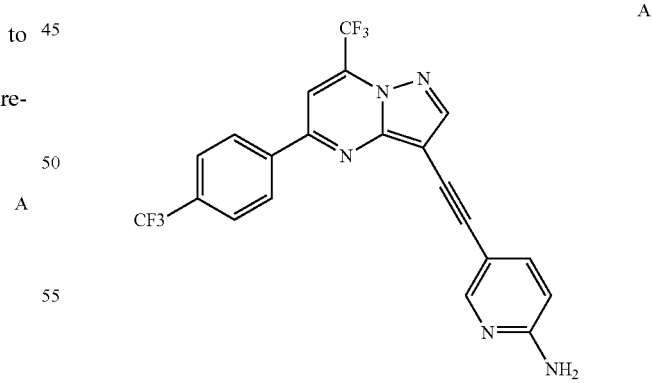

which comprise:
(a) dissolving crude compound A in tetrahydrofuran to form a solution;
(b) treating the solution from step (a) with n-tributylphosphine;
(c) adding methanesulfonic acid to the reaction mixture from step (b) to precipitate a mesylate salt of compound A (compound A-1);

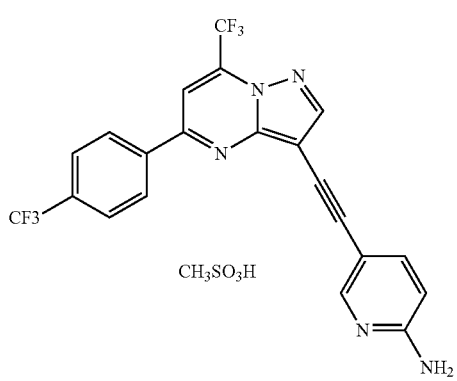

(d) isolating the mesylate salt from step (c);
(e) slurrying the mesylate salt from step (d) in 2-methyltetrahydrofuran to form an organic mixture;
(f) treating the organic mixture from step (e) with aqueous sodium carbonate to convert the mesylate salt A-1 to compound A, resulting in an aqueous phase and an organic phase containing compound A;
(g) separating the aqueous and organic phases from step (f) and washing the organic phase with water; and
(h) conducting a solvent exchange on the organic phase to replace 2-methyltetrahydrofuran by isopropanol to provide pure crystalline compound A.

The present invention further provides methods for preparing compound 3 or 7 having the formula:

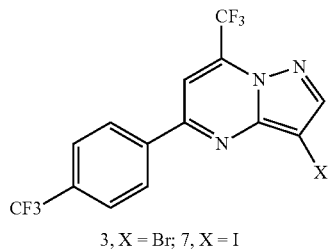

which comprise:
(a) reacting compound 1;

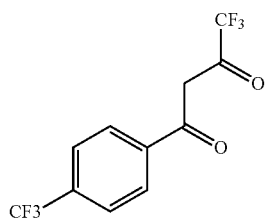

with compound 10;

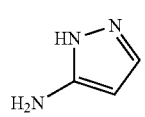

via a condensation reaction to provide compound 11;

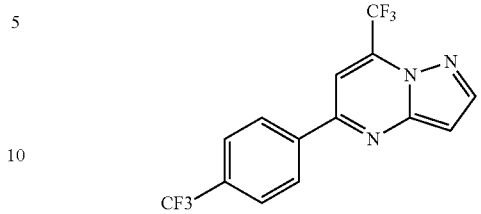

and
(b) reacting compound 11, with a halogenating agent to provide compound 3 or 7.

The present invention further provides methods for preparing compound 9 having the formula:

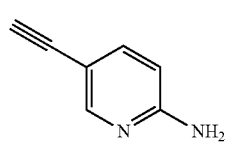

which comprise:
(a) reacting compound 6 or 8;

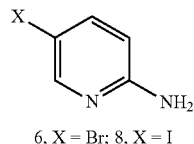

6, X = Br; 8, X = I with trimethylsilylacetylene via a Sonogashira coupling reaction in an inert solvent to provide compound 12;

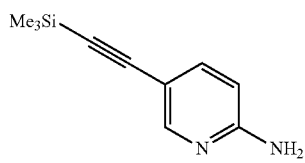

and
b) desilylating compound 12 in an inert solvent to provide compound 9.

The present invention further provides methods for preparing compound 9 having the formula:

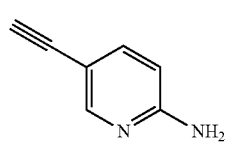

which comprises:
(a) reacting compound 6 or 8;

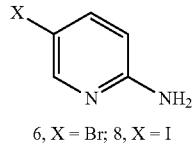

6, X = Br; 8, X = I with 2-methyl-3-butyn-2-ol via a Sonogashira coupling reaction in an inert solvent to provide compound 13;

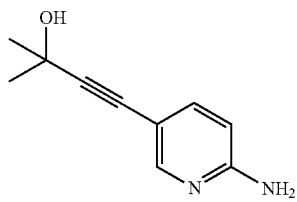

13 and
b) deprotecting compound 13 with a base in an inert solvent to provide compound 9.

The present invention further provides methods for preparing compound 7 having the formula:

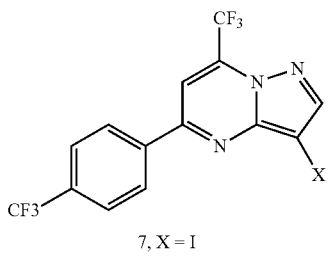

7, X = I which comprise:
(a) reacting compound 14;

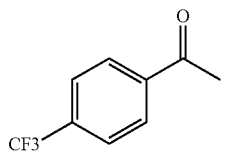

14 with ethyl trifluoroacetate under basic conditions in an inert solvent to provide intermediate compound 15;

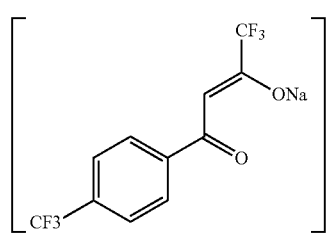

15 b) reacting intermediate compound 15 with 3-aminopyrazole in an inert solvent to provide intermediate compound 11;

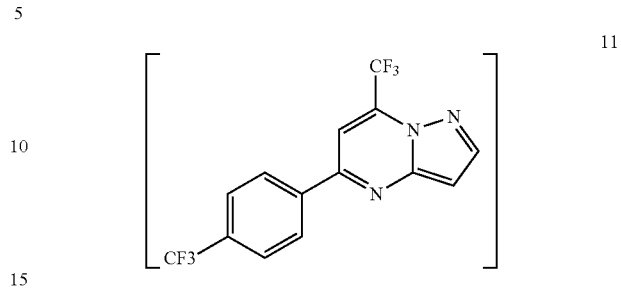

11 and
c) reacting intermediate compound 11 with an iodinating agent under acidic conditions to provide compound 7.

DETAILED DESCRIPTION OF THE INVENTION

The present invention provides methods for preparing 5-[2-[7-(trifluoromethyl)-5-[4-(trifluoromethyl)phenyl]pyrazolo[1,5-a]pyrimidin-3-yl]ethynyl]-2-pyridinamine (compound A). The present methods are useful for preparing compound A on large scale in manufacturing facilities.

As used herein, the following terms have the meanings set out below.

The term "acidic conditions" refers to conditions relating to the pH value of an aqueous solution. Pure water is considered to be neutral, with a pH close to 7.0 at 25° C. Solutions with a pH value less than 7 are considered to be acidic solutions or conditions.

The term "$C_{1-6}$-alkyl" refers to a monovalent linear or branched saturated hydrocarbon group of 1 to 6 carbon atoms, for example, methyl, ethyl, propyl, isopropyl, n-butyl, iso-butyl, sec-butyl, or tert-butyl.

The term "aryl" refers to a monovalent aromatic carbocyclic mono- or bicyclic ring system comprising 6 to 10 carbon ring atoms. Examples of aryl moieties include phenyl and naphthyl.

The term "basic conditions" refers to conditions relating to the pH value. Pure water is considered to be neutral, with a pH close to 7.0 at 25° C. Solutions with a pH value greater than 7 are considered to be basic or alkaline solutions or conditions.

The term "condensation reaction" refers to a chemical reaction in which two molecules or moieties (functional groups) combine to form one single molecule, together with the loss of a small molecule. When this small molecule is water, the reaction is known as a dehydration reaction.

The term "desilylating" refers to the removal of silyl protecting groups in a molecule. Fluoride ions, such as those present in potassium fluoride, KF, are useful for removal of silyl protecting groups in desilylation reactions.

The term "halogen" refers to chloro, bromo, iodo and fluoro, and is preferably iodo and bromo.

The term "halogenating agent" refers to an agent used in a halogenation reaction that incorporates a halogen atom into a molecule. Specific types of halogenating agents include fluorinating, chlorinating, brominating, and iodinating agents. Non-limiting illustrative halogenating agents include N-bromosuccinimide (NBS), iodine chloride (ICl), N-iodosuccinimide (NIS), and mixed agents such as $I_2/NaIO_4/HCl$.

The term "hydrolyzing" refers to a hydrolysis reaction (hydrolysis) in which a parent molecule is split into two parts by the addition of a molecule of water. During the hydrolysis reaction, molecules of water are split into hydrogen cations (H+) and hydroxide anions (OH−). One fragment of the parent molecule gains a hydrogen cation from the water molecule; the other fragment gains the hydroxide anion.

The term "inert organic solvent" refers to a solvent that does not interfere chemically with the reaction. Illustrative, non-limiting examples of inert organic solvents in the present invention include tetrahydrofuran, 2-methyltetrahydrofuran, dimethylformamide, toluene, tert-butyl methyl ether, and the like.

The term "intermediate compound" refers to a compound, which is produced during the course of a chemical synthesis. An intermediate compound is not itself, the final product, but is used in further reactions, which produce the final product. This is in contrast to the starting material and final product. An intermediate compound may be isolated or not. Often it is not isolated or purified but rather is used "as is" in the synthesis for economic reasons especially on industrial scale.

The term "mesylate" (mesilate) refers to a salt or ester of methanesulfonic acid, $CH_3SO_3H$. In salts, the mesylate is present as the $CH_3SO_3^-$ anion.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hydroscopicity, and solubility of compounds. See, e.g., H. Ansel et. al., Pharmaceutical Dosage Forms and Drug Delivery Systems (6th Ed, 1995) at pp. 196 and 1456-1457.

The term "protective group" refers to a group introduced into a molecule by chemical modification in order to obtain chemoselectivity in a subsequent chemical reaction. In many preparations of organic compounds, some functional groups in the molecule cannot survive the reaction reagents or chemical environment. These functional groups must therefore be protected with a protective group, which will protect the functional group during such a reaction. The protective group is generally easily removed (deprotection) after the chemical reaction. Protective groups play an important role in multi-step organic synthesis. One skilled in the art would readily know how to protect and deprotect a particular functional group. Many text books and other references provide such resources including "Protective Groups in Organic Chemistry", J. F. W. McOmie, Plenum Press, 1973; "Greene's Protective Groups in Organic Synthesis", 4th Edition, Peter G. M. Wuts and Theodora W. Greene, 2006; Wiley, amongst others.

The term "Sonogashira coupling reaction" refers to a coupling reaction of terminal alkynes with aryl or vinyl halides. Typically, two catalysts are needed for this reaction: a zerovalent palladium complex and a halide salt of copper (I). The palladium complex activates the organic halides by oxidative addition into the carbon halogen bond. Phosphine-palladium complexes such as tetrakis(triphenylphosphine) palladium(0) or bis-(triphenylphosphine)-palladium(II)-dichloride are typically used for this reaction. Copper (I) halides react with the terminal alkyne and produce copper (I) acetylide, which acts as an activated species for the coupling reaction. The reaction medium must be basic to neutralize the hydrogen halide produced as the byproduct of this coupling reaction. Alkylamine compounds such as triethylamine, diethylamine, or diisopropylamine may be used as bases.

The term "water-scavenging agent" or dehydrating agent refers to an agent that is used to remove water from a reaction mixture in order to accelerate the rate of the reaction. The agent 1,1,1,3,3,3-hexamethyldisilazane (HMDS) is often used as a water-scavenging agent to enable coupling reactions to proceed faster and cleaner.

The present invention provides methods for preparing compound A. One method employs the coupling of compound 5 with 2-amino-5-halopyridine (compound 6 or 8), as illustrated in Scheme 1.

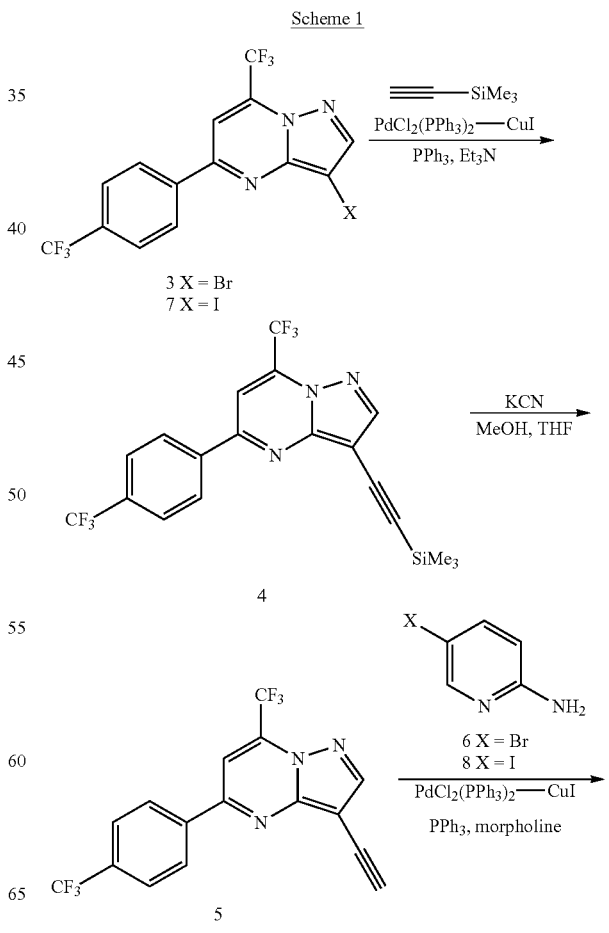

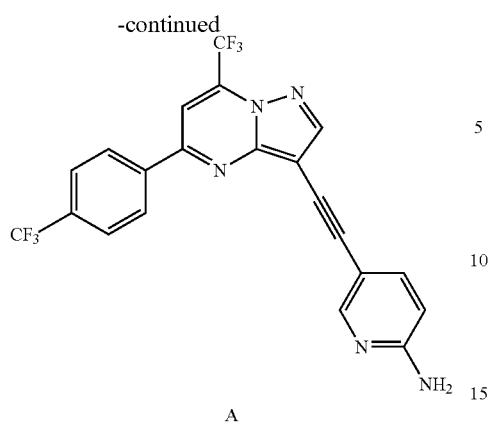

A

The methods in Scheme 1 comprise: (a) coupling compound 3 or 7 with trimethylsilylacetylene using a Sonogashira coupling reaction to provide compound 4; (b) desilylating compound 4 to afford compound 5; and (c) coupling compound 5 with compound 6 or 8 using a Sonogashira coupling reaction to provide compound A.

In one embodiment, the invention provides a method for preparing compound A which comprises reacting compound 5 with compound 6 or 8 via a Sonogashira coupling reaction in an inert solvent to provide compound A. In another embodiment, the invention provides a method wherein compound 5 is prepared by desilylating compound 4 in an inert solvent. In another embodiment, the invention provides a method wherein compound 4 is prepared by reacting compound 3 or 7 with trimethylsilylacetylene via a Sonogashira coupling reaction in an inert solvent.

Scheme 1 is presented with preferred reagents and conditions. A broad range of conditions can be applied in a Sonogashira reaction. For instance, while trimethylsilylacetylene is the preferred reagent for the preparation of 5, other silyl group protected acetylenes, with a general structure set out below, can also be used in place of trimethylsilylacetylene.

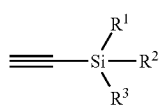

where $R^1$, $R^2$, and $R^3$ can be simple alkyl groups, such as ethyl, n-propyl, and n-butyl; or can also be simple aryl groups, such as a phenyl group.

While $Pd(Ph_3P)_2Cl_2$ is the preferred catalyst for the reaction, other types of palladium catalysts can also be used. Nonlimiting examples of such catalysts include $Pd_2(dba)_3$, $Na_2PdCl_4$, and $Pd(OAc)_2$.

While $Ph_3P$ is the preferred ligand for the reaction, other types of ligands can also be used. Nonlimiting examples of such ligands include $P(t-Bu)_3$, $P(o-Tol)_3$, and other non-phosphorous ligands.

While $NEt_3$ is the preferred base for the reaction, other types of bases can also be used in the reaction. Nonlimiting examples of such bases include $Et_2NH$, pyrrolidine, i-$Pr_2NH$, diisopropylethylamine, morpholine, and $Cs_2CO_3$.

A variety of solvents can be used in Sonogashira reaction, such as DMF, THF, 2-Me-THF, $CH_3CN$, DMSO, toluene, and 1,4-dioxane.

While KCN is the preferred reagent for conversion of 4 to 5, other reagents can also be used for the de-protection. Nonlimiting examples of such reagents include hydroxide, alkoxides, HF, KF, NaF, $Bu_4NF$, and other HF-amine salts. A wide range of solvents can be used for the reaction.

The conditions (Sonogashira reaction) that can be used for conversion of 5 to A, and for all of the Sonogashira reactions described herein, are similar to those for the conversion of 3/7 to 4.

The present invention provides other methods for preparing compound A, as illustrated in Scheme 2.

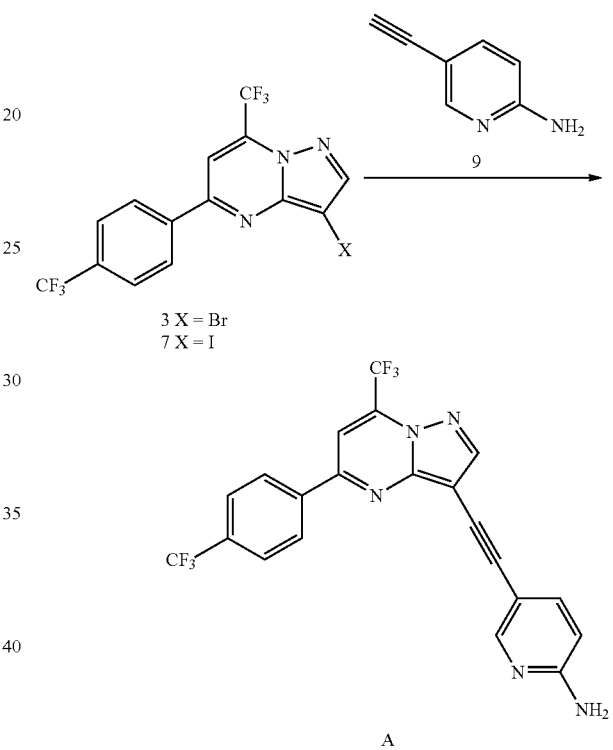

In Scheme 2, compound 3 or 7 is coupled with 2-amino-5-ethynyl-pyridine (compound 9) using a Sonogashira coupling reaction to provide compound A. The range of conditions that can be employed are similar to those for Scheme 1.

The invention also includes methods for preparing compound 3 and 7, as illustrated in Scheme 3.

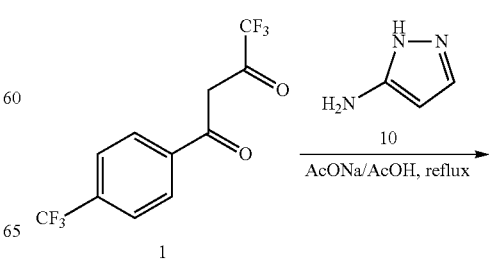

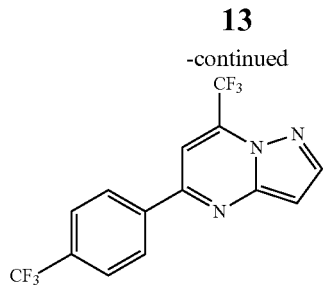

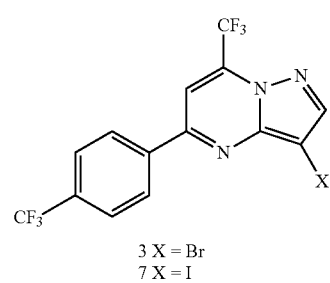

3 X = Br
7 X = I

The methods in Scheme 3 comprise: (a) condensing compound 1 with 3-aminopyrazole (compound 10) to form compound 11; (b) reacting compound 11 with N-bromosuccinimide (NBS) to provide compound 3; or alternatively, (c) reacting compound 11 with iodine chloride (ICl) to provide compound 7; or alternatively, (d) reacting compound 11 with N-iodosuccinimide (NIS) to provide compound 7; or alternatively, (e) reacting compound 11 with a mixed reagent of $I_2/NaIO_4/HCl$ to provide compound 7.

In one embodiment, the invention provides a method for preparing compound, which comprises reacting compound 11, with a halogenating agent to provide compound 3 or 7. In yet another embodiment, the halogenating agent is N-bromosuccinimide to provide compound 3, iodine chloride to provide compound 7, N-iodosuccinimide to provide compound 7, or $I_2/NaIO_4/HCl$ to provide compound 7. In yet another embodiment, the compound 11 is prepared by reacting compound 1 with compound 10 via a condensation reaction to provide compound 11.

Other reagents can also be used for the conversion of 1 to 11, for example NaOEt/HOEt, AcOH/refluxing, and toluene/distillation.

The invention also includes methods for preparing compound 9, as illustrated in Scheme 4.

Scheme 4

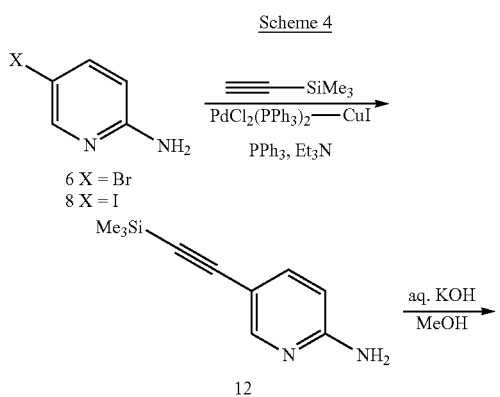

The methods in Scheme 4 comprise: (a) coupling compound 6 or 8 with trimethylsilylacetylene using a Sonogashira coupling reaction to provide compound 12; and (b) desilylating compound 12 to provide compound 9.

The invention also includes methods for preparing compound 9, as illustrated in Scheme 5.

Scheme 5

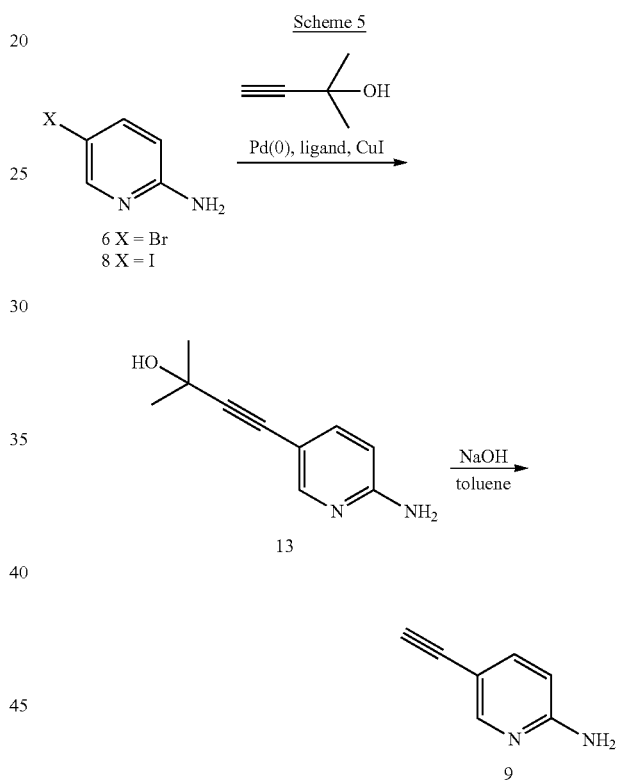

The methods in Scheme 5 comprise: (a) coupling compound 6 or 8 with 2-methyl-3-butyn-2-ol using a Sonogashira coupling reaction to provide compound 13; and (b) deprotecting compound 13 to provide compound 9.

For the deprotection, strong bases other than NaOH can also be used. Nonlimiting examples of such bases include $Na_2CO_3$, $K_2CO_3$, KOH, K(or Na)OMe, K(or Na)OEt, and K(or Na)Ot-Bu or combinations thereof. Any non-acidic solvent that is stable under strong basic conditions can be used for the reaction, including, but not limited to, simple alcohols, ethers, and hydrocarbons.

The invention also includes a "one-pot" method (without isolation of the intermediates 15 and 11) for preparing compound 7 starting from 4'-(trifluoromethyl) acetophenone (compound 14), as illustrated in Scheme 6.

Scheme 6

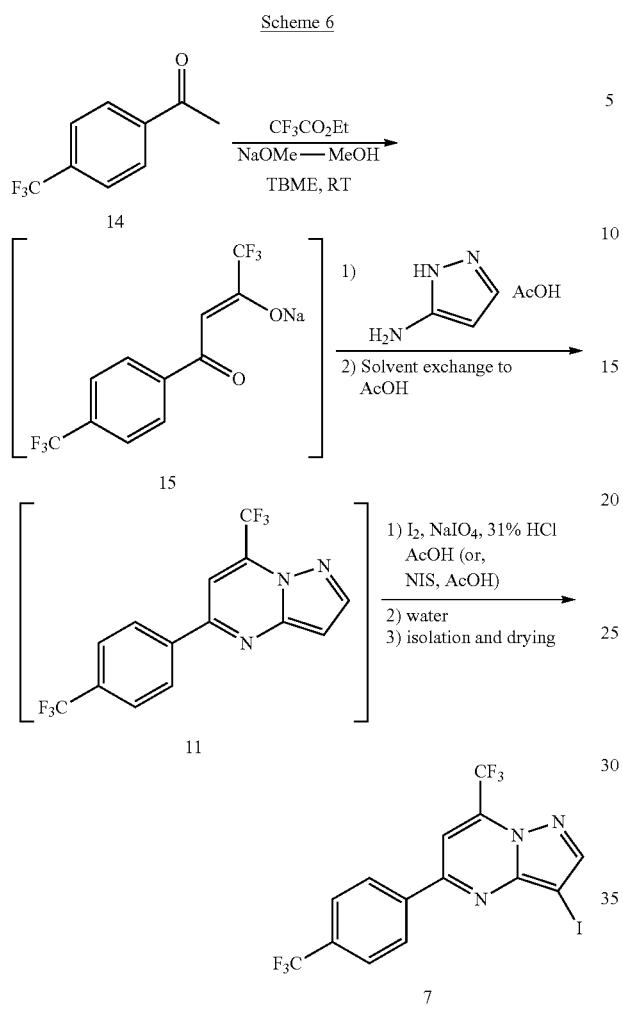

Scheme 7

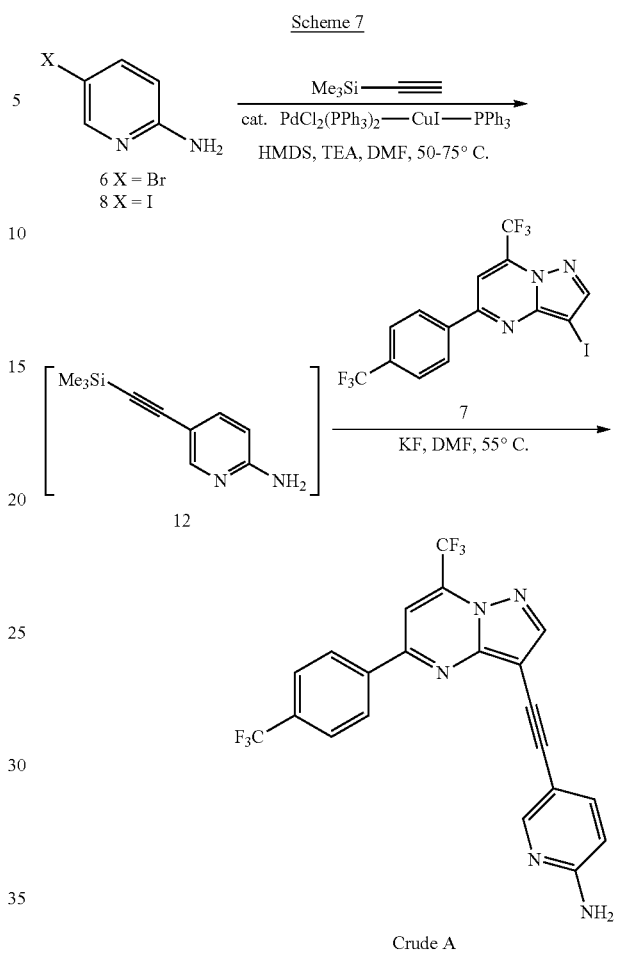

The method in Scheme 6 comprises: (a) reacting compound 14 with ethyl trifluoroacetate in NaOMe/MeOH and t-butyl methyl ether (methyl t-butyl ether, TBME, MTBE) to provide intermediate compound 15; (b) mixing intermediate compound 15 with 3-aminopyrazole in acetic acid to provide intermediate compound 11; and (c) mixing intermediate compound 11 with a mixture of $I_2$/NaIO$_4$/31% HCl (or NIS) in acetic acid to provide compound 7. This "one-pot" method is cost effective and efficient because workup and isolation of the intermediates are eliminated, resulting in the reduction of solvent usage and manufacturing time.

In one embodiment, the invention provides a method for preparing compound 7, which comprises reacting compound 11 with an iodinating agent under acidic conditions to provide compound 7. In yet another embodiment, the iodinating agent is N-iodosuccinimide or $I_2$/NaIO$_4$/HCl. In yet another embodiment, compound 11 is prepared by reacting compound 15 with 3-aminopyrazole in an inert solvent to provide compound 11. In yet another embodiment, compound 15 is prepared by reacting compound 14 with ethyl trifluoroacetate under basic conditions in an inert solvent to provide compound 15.

The present invention further provides processes for preparing compound A, as illustrated in Scheme 7, which advantageously can be performed as "one-pot" methods (without isolation of compounds 12 and 9).

The methods in Scheme 7 comprise: (a) reacting compound 6 or 8 with trimethylsilylacetylene using a Sonogashira coupling reaction to provide intermediate compound 12; (b) reacting intermediate compound 12 with KF to desilylate compound 12 to compound 9, in situ; and (c) reacting compound 9 with compound 7 through a second Sonogashira coupling reaction to provide compound A. Although not required, HMDS (1,1,1,3,3,3-hexamethyldisilazane) is preferably used as a water-scavenging agent in step (a) to make the coupling reaction faster and cleaner.

In one embodiment, the invention provides a method for preparing compound A having the formula which comprises reacting compound 12 with compound 7 in an inert solvent in the presence of potassium fluoride to provide compound A. The reaction of compound 12 with compound 7 is preferably carried out in the presence of a water-scavenging agent, such as 1,1,1,3,3,3-hexamethyldisilazane. In yet another embodiment, compound 1:2 is prepared reacting compound 6 or 8 with trimethylsilylacetylene via a Sonogashira coupling reaction in an inert solvent to provide compound 12. In yet another embodiment, compound 12 is prepared by reacting compound 6 or 8 with trimethylsilylacetylene via a Sonogashira coupling reaction in an inert solvent to provide compound 12.

This "one-pot" method in Scheme 7 offers several advantages. For example, the isolation of intermediate compounds 12 and 9 is avoided. Two Sonogashira coupling reactions are carried out using one set of the catalyst system [PdCl$_2$ (PPh₃)₂-CuI]. Preferably, water is added to the mixture at the end of step (c) to precipitate crude compound A.

The present invention provides further methods for preparing compound A, as illustrated in Scheme 8.

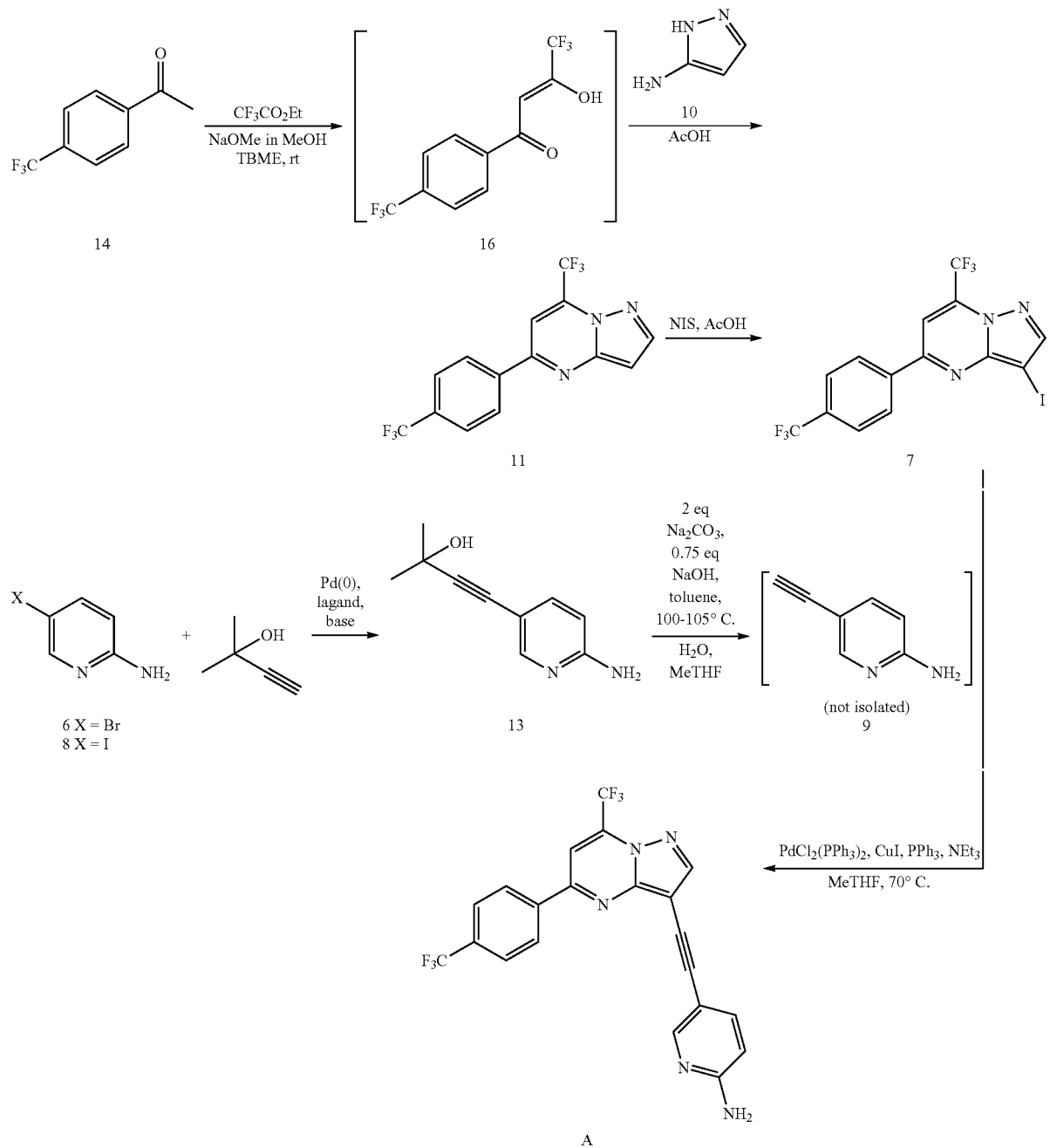

Scheme 8

The method in Scheme 6 comprises: (a) coupling compound 7 with compound 9 using a Sonogashira coupling reaction to provide crude compound A, which then can be purified, for example, by recrystallization in a mixture of 2-methyltetrahydrofuran and isopropyl alcohol.

The method for preparing compound 7 comprises: (a) reacting compound 14 with ethyl trifluoroacetate in NaOMe/ MeOH and t-butyl methyl ether (methyl t-butyl ether, TBME, MTBE) at room temperature to provide intermediate compound 16; (b) mixing intermediate compound 16 with 3-aminopyrazole in acetic acid to provide intermediate compound 11; (c) mixing intermediate compound 11 with N-iodosuccinimide (NIS) in acetic acid to provide intermediate compound 7.

The method for preparing compound 9 comprises: (a) coupling of a 2-amino-5-halopyridine (compound 6 or 8) with 2-methyl-3-butyn-2-ol via a Sonogashira coupling reaction to provide compound 13 and (b) deprotecting compound 13 to provide compound 9.

A method for preparing compound 13 from Compound 8 is provided in Scheme 9.

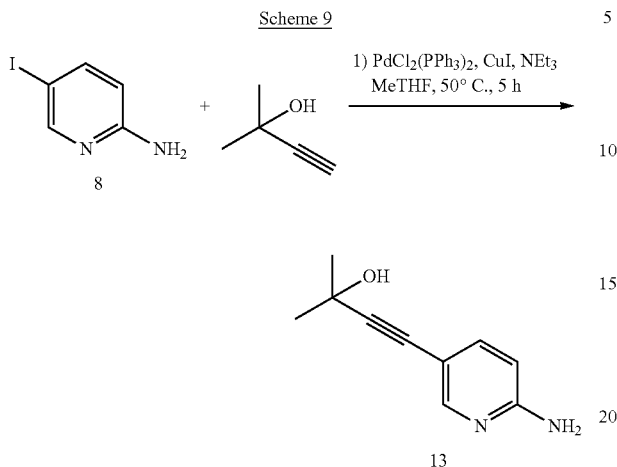

In one embodiment, the preparation of compound 13 comprises (a) reacting 2-amino-5-iodopyridine 8 with 2-methyl-3-butyn-2-ol in a Sonogashira coupling reaction, employing a PdCl$_2$(PPh$_3$)$_2$-CuI catalyst with triethylamine as base in tetrahydrofuran or 2-methyltetrahydrofuran at a temperature of about 50° C. for approximately 5 hours.

A method for preparing compound 13 from Compound 6 is provided in Scheme 10.

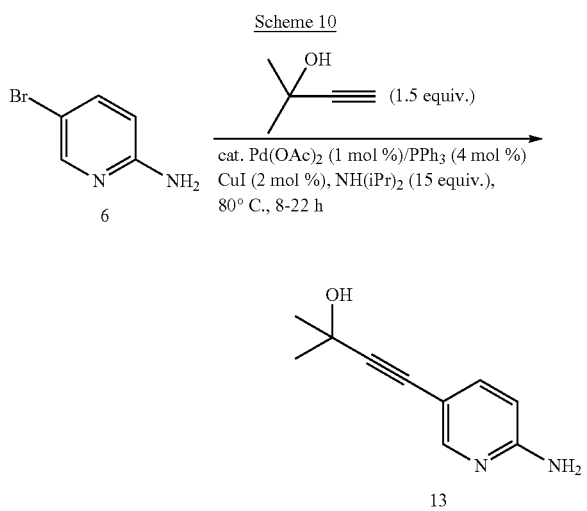

In another embodiment, the preparation of compound 13 comprises (a) reacting a mixture of 2-amino-5-bromopyridine 6; 2-methyl-3-butyn-2-ol; and a Pd(OAc)$_2$/PPh$_3$-CuI catalyst in di-isopropylamine at a temperature of about 80° C. for a period of 8 to 2.2 hours.

Compound A may contain impurities, such as palladium copper salts and organic and inorganic impurities. The present invention provides novel purification methods for purifying compound A, as illustrated in Scheme 11.

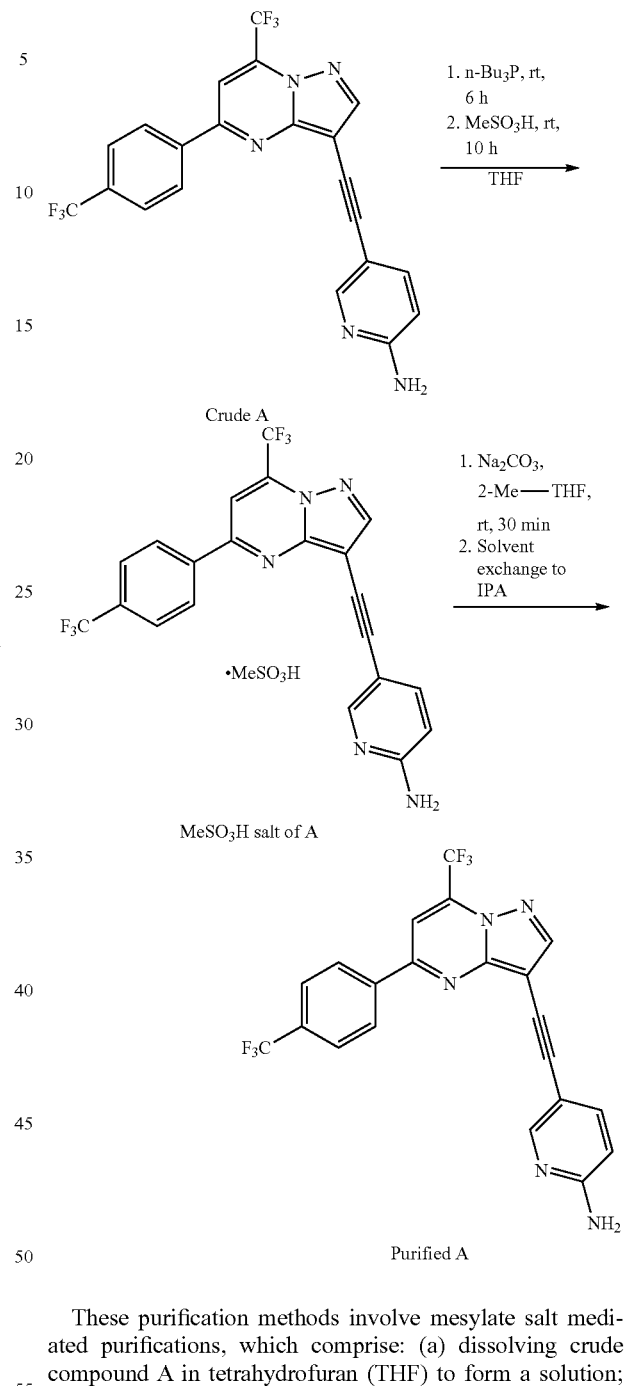

These purification methods involve mesylate salt mediated purifications, which comprise: (a) dissolving crude compound A in tetrahydrofuran (THF) to form a solution; (b) treating the solution from step (a) with n-tributylphosphine to remove palladium and copper; (c) adding methanesulfonic acid to the reaction mixture from step (b) to form a mesylate salt of compound A (compound A-1), which precipitates from solution; (d) isolating the mesylate salt from step (c); (e) slurrying the mesylate salt from step (d) in 2-methyltetrahydrofuran (2-Me-THF); (f) treating the organic 2-methyltetrahydrofuran reaction mixture from step (e) with aqueous sodium carbonate to convert the mesylate salt to the free base of compound A, resulting in an aqueous phase and an organic phase containing the free base of compound A; (g) separating the aqueous and organic phases and washing the organic phase with water; and (h) conducting a solvent exchange on the organic phase from 2-Me-THE to isopropanol (IPA) to provide pure crystalline compound A.

In one embodiment, the invention provides a method for preparing compound A-1 having the formula

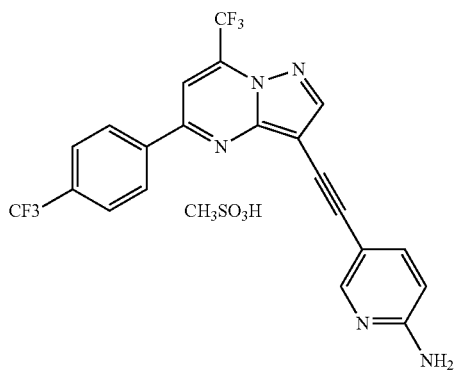

A-1 which comprises (a) dissolving compound A in tetrahydrofuran to form a solution; (b) treating the solution from step (a) with n-tributylphosphine; and (c) adding methanesulfonic acid to the reaction mixture from step (b) to precipitate compound A-1.

In yet another embodiment, the invention provides a method for purifying compound A which comprises (a) slurrying compound A1 in 2-methyltetrahydrofuran to form an organic mixture; (b) treating the organic mixture from step (a) with an aqueous alkaline solution to convert compound A4 to free base compound A; (c) separating the aqueous and organic phases from step (b) and washing the organic phase with water; and (d) separating and concentrating the organic phase from step (c) to provide purified compound A. Preferably, the aqueous alkaline solution is an aqueous sodium carbonate solution. Preferably, the method further comprises conducting a solvent exchange on the organic phase after step (c) to convert the solvent to isopropanol to provide crystalline compound A.

While n-tributylphosphine is the most effective reagent for removing palladium and copper, many other phosphines with a formula of $PR_3$ where R can be simple alkyl groups (e.g. Me, Et, n-propyl, etc.) or aryl groups (e.g. phenyl, p-tolulyl, etc.) can be used in the present reaction.

While methanesulfonic acid is the preferred acid for the salt formation, many other acids can be used. Nonlimiting examples of such acids include HCl, p-TsOH, $H_2SO_4$, $H_3PO_4$, and HBr.

While THF is the preferred solvent for the conversion, many other inert solvents can also be used. Nonlimiting examples of such solvents include 2-MeTHF, ethyl acetate, methyl t-butyl ether, and acetonitrile.

While sodium carbonate is the preferred base for the conversion of $MeSO_3H$ salt of A to pure A, other bases can also been used. Nonlimiting examples of such bases include KOH, NaOH, $K_2CO_3$, and $Cs_2CO_3$.

While 2-Me-THF is the preferred solvent for the conversion, many other inert solvents can also be used. Nonlimiting examples of such solvents include THF, ethyl acetate, and methyl t-butyl ether.

The compounds of the present invention can be prepared according to the examples set out below. The examples are presented for purposes of demonstrating, but not limiting, the preparation of the compounds of this invention.

EXAMPLES

In accordance with the present invention, the following examples are provided to illustrate preferred methods for the preparation of the compounds of this invention.

Example 1

This example illustrates a method for the preparation of compound 4.

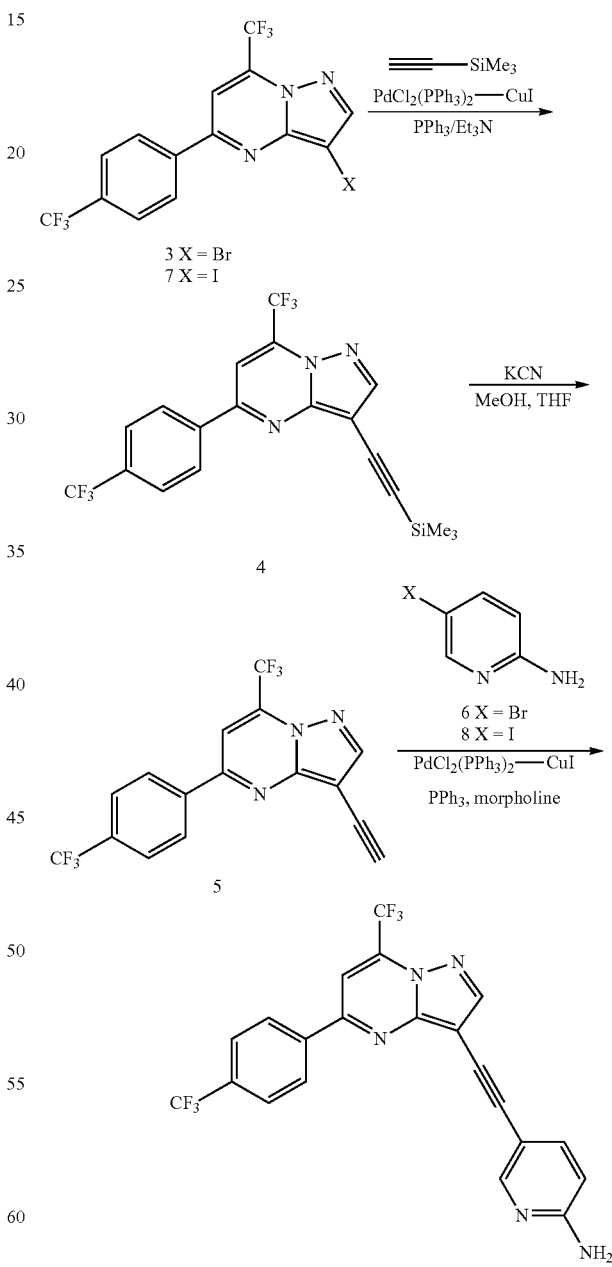

A solution of 3 (1.64 g, 4 mmol), trimethylsilylacetylene (1.13 mL, 8 mmol), copper(I) bromide dimethylsulphide complex (34 mg, 0.16 mmol), palladium(II) acetate (19 mg, 0.08 mmol), triphenylphosphine (87 mg, 0.32 mmol) in degassed triethylamine (16 mL) was stirred under an argon atmosphere at 50° C. for 22 h. The brown suspension was diluted with ethyl acetate (EtOAc, 20 mL) and evaporated under reduced pressure (200-20 mb) at 45° C. The residue was distributed between EtOAc (20 mL) and water (20 mL) and filtered through a glass-sintered funnel to remove insoluble material. The organic layer was separated, washed with water (20 mL), the aqueous phases back extracted with EtOAc (20 mL) and the combined organic extracts were dried over sodium sulphate ($Na_2SO_4$), filtered and evaporated. The brown residue (2.0 g) was purified by dissolution in acetic acid (AcOH, 12 mL) at 70° C. and precipitation by the addition over 5 min. of water (5 mL). The thick orange suspension was cooled and stirred at room temperature (RT) for 1 h then filtered. The product 4 was washed twice with aqueous AcOH (1:1, 3 mL) and once with water (5 mL). After drying at 45° C./20 mb for 2 h, 1.68 g (98%, GLC 96%, HPLC 89% purity) of orange crystalline solid compound 4 was obtained.

Example 2

This example illustrates another method for the preparation of compound 4.

A solution of 7 (3.66 g, 8 mmol), trimethylsilylacetylene (2.26 mL, 16 mmol), copper(I) bromide dimethylsulphide complex (67 mg, 0.32 mmol), palladium(II) acetate (37 mg, 0.16 mmol), triphenylphosphine (173 mg, 0.64 mmol) in degassed triethylamine (30 mL) was stirred under an argon atmosphere at 50° C. for 20 h. The brown suspension was diluted with ethyl acetate (EtOAc, 20 mL) and evaporated under reduced pressure (200-20 mb) at 45° C. The residue was distributed between EtOAc (20 mL) and water (20 mL) and filtered through a glass-sintered funnel to remove insoluble material. The organic layer was separated, washed with water (20 mL), the aqueous phases back extracted with EtOAc (20 mL) and the combined organic extracts were dried over $Na_2SO_4$, filtered and evaporated. The brown residue (3.7 g) was purified by dissolution in AcOH (22 mL) at 100° C. and precipitation by the addition over 10 min. of water (8 mL). The thick orange suspension was cooled and stifled at RT for 1 h, then filtered. The product 4 was washed twice with aqueous AcOH (1:1, 10 mL) and twice with water (10 mL). After drying at 4.5° C./20 mb for 16 h, 3.0 g (87%, GLC 97% purity) of orange crystalline solid compound 4 was obtained.

Example 3

This example illustrates a method for the preparation of compound 5.

Intermediate 4 (3.0 g, 7 mmol) was dissolved in a mixture of THF (8 mL) and MeOH (12 mL). Potassium cyanide (0.49 g, 7.3 mmol) was added and the dark brown solution was stirred under an argon atmosphere at RT for 16 h then evaporated under reduced pressure. The residue was distributed between EtOAc (20 mL) and water (20 mL). The organic phase was separated and washed with water (20 mL), dried over $Na_2SO_4$, filtered and evaporated under reduced pressure. The residue (2.82 g) was purified by dissolution AcOH (21 mL) at RT and precipitation by the addition over 10 min. of water (7 mL). The beige suspension was stirred at RT for 1 h, then filtered. The product 5 was washed twice with aqueous AcOH (1:1, 10 mL) and twice with water (10 mL). After drying at 45° C./20 mb for 16 h, 2.0 g (80%, HPLC 96% purity) of beige crystalline solid compound 5 was obtained. The filtrate was refiltered affording additional material (0.3 g, 11%, HPLC 77%) of compound 5.

Example 4

This example illustrates a method for the preparation of compound A.

Acetylene 5 (53 mg, 0.15 mmol) was dissolved in degassed morpholine (1 ml) and treated consecutively with 2-amino-5-iodopyridine (35 mg 0.16 mmol), tetrakis(triphenylphosphine)palladium (4 mg, 0.003 mmol) and copper(I) bromide dimethylsulphide complex (1 mg, 0.006 mmol). The brown solution was stirred under an argon atmosphere at 75° C. for 0.5 h then distributed between EtOAc (10 mL) and water (10 mL). The organic layer was separated, the aqueous phase extracted with EtOAc (5 mL) and the combined organic extracts were washed with water (5 mL) then dried over $Na_2SO_4$, filtered and evaporated yielding a red-brown residue (80 mg) of compound A. HPLC analysis indicated 95% purity of compound A.

Example 5

This example illustrates a method for the preparation of crude compound A and its purification via the HCl-salt of compound A.

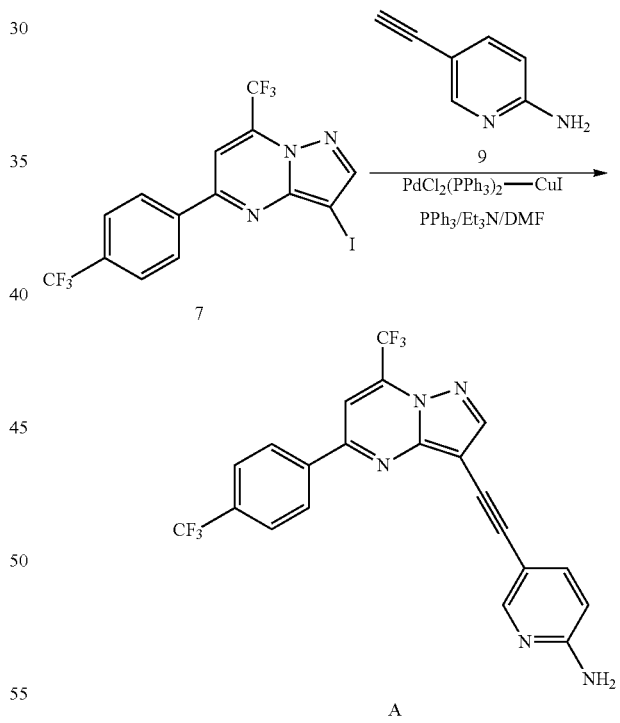

A 1.5 L 4-necked round bottom flask equipped with a thermometer, a mechanical stirrer and an inert gas supply, were charged with 67.3 ml triethylamine (483.3 mmol, 2.6 eq.), 1.33 g (1.86 mmol, 0.01 eq.) bis-(triphenylphosphine)-palladium(II)-dichloride, 1.03 g (3.72 mmol, 0.02 eq.) triphenylphosphine, 0.37 g (1.9 mmol, 0.01 eq.) copper(I) and 170 ml DMF. The mixture was heated to 75° C., producing a dark brown solution. To this solution was added a solution of 85 g (185.9 mmol) 7 and 24.16 g (204.5 mmol, 1.1 eq.) 9 in 340 ml DMF containing 2.6 ml (18.6 mmol, 0.1 eq.)

triethylamine over 1 h at 68-72° C. through an addition funnel. The addition funnel was rinsed with 40 ml DMF and stirring was continued for 16 h until the reaction was completed. The resulting dark red suspension was evaporated under reduced pressure (120-50 mbar) at 80° C., removing ~170 ml of solvent. Crystallization was initiated by adding 850 ml water at room temperature over ~0.5 h. The red suspension was stirred at room temperature for 19 h, filtered, washed with 500 ml water, then dried at 50° C. under <10 mbar for 48 h yielding 87.3 g (84%) of crude compound A.

A quantity of 70 g of crude A was dissolved in 650 ml THF. The solution was diluted with 650 mL t-butyl methyl ether and filtered through 490 g neutral aluminum oxide III, eluting with a mixture prepared from 1300 mL THF and 1300 mL t-butyl methyl ether. The filtrate was concentrated to a volume of 400 mL. Thereafter, 325 mL THF were added with constant volume distillation. N-Acetyl-L-cysteine, 3.5 g (21.2 mmol, 0.14 eq.), was added and the solution was stirred at room temperature for 1 h. 45 mL (180 mmol, 1.15 eq.) 4N Hydrogen chloride were added and stirring was continued at room temperature for 16 h. The crystalline suspension formed was filtered and the yellow wet cake was washed with 150 mL t-butyl methyl ether to give the HCl-salt of compound A.

A suspension of 100 g (207 mmol) of the crude HCl-salt of compound A in 700 mL THF was treated with a solution of 34.8 g (414 mmol, 2 eq.) sodium carbonate in 600 mL water. Over 0.5 h, an additional 800 mL of water was added and crystallization was completed at room temperature for 2 h. The product was filtered and washed with a mixed solvent of 150 mL THF and 300 mL water, followed by 300 mL water and then 200 mL 2-propanol. The wet cake product was dissolved in 1480 mL acetone and the solution was concentrated to a volume of 470 mL. Subsequently, 600 mL 2-propanol were added with constant volume distillation. The crystalline suspension was stirred at room temperature for 16 h, filtered, washed with 600 mL 2-propanol then dried at 50° C. under <10 mbar for 24 h providing pure compound A.

Example 6

This example illustrates a method for the preparation of compound A.

A solution of 7 (36.0 g), copper(I) iodide (334 mg), bis-(triphenylphosphine)-palladium(II)-dichloride (557 mg), triphenylphosphine (414 mg) and triethylamine (25.5 mL) in MeTHF (145 mL) was treated at 70-75° C. within 2 to 3 hours with a MeTHF solution of 1.1 equiv. of 5-ethynylpyridin-2-ylamine (9) (prepared according to Example 11) and the resulting suspension was subsequently stirred at 70-75° C. for additional 5-10 hours. The mixture was cooled to 30° C. and treated with water (150 mL) and 25% aqueous ammonium hydroxide solution (30 mL). The biphasic mixture was stirred for 30 minutes and the layers were then allowed to separate for 20 minutes. The aqueous layer was removed and the MeTHF layer was washed twice with a mixture of water (150 mL) and 25% aqueous ammonium hydroxide solution (30 mL). The MeTHF layer was subsequently washed with water (3×150 mL). The organic layer was polish filtered, and the filtrate was treated with n-tributylphosphine (1.00 mL). MeTHF was then distilled off and completely replaced by isopropanol (500 mL in total) at atmospheric pressure. The resulting suspension (ca. 250 mL) was heated to reflux and stirred at reflux for 2 hours then cooled to room temperature overnight. The product was filtered and washed with two portions of isopropanol (50 mL). The wet crystals were dried at 50° C. and <30 mbar until constant weight affording 29.45 g (84% yield based on 7) of compound A as red crystals with a purity of 99.7% (HPLC, area-%).

Example 7

This example illustrates a method for the preparation of compound 7.

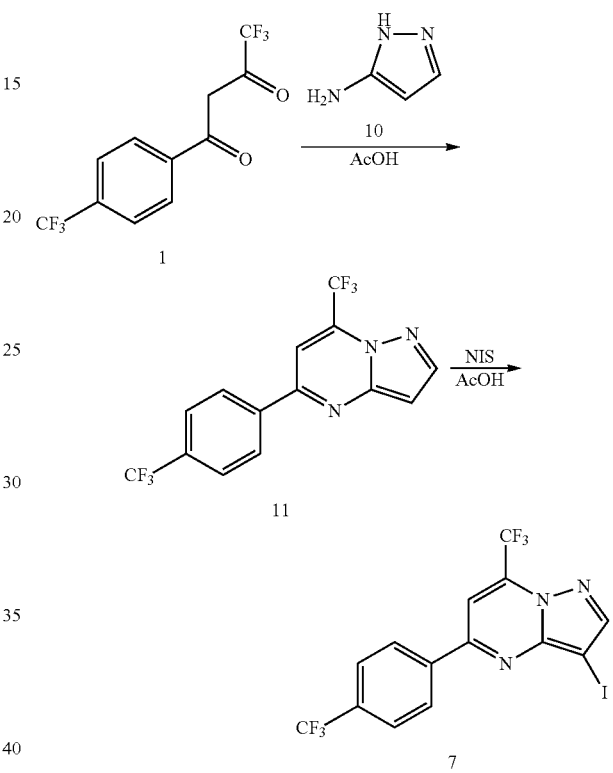

A 1.5 L 4-necked round bottom flask equipped with a thermometer, a mechanic stirrer and an inert gas supply, were charged a solution of 1 (85.2 g, 300 mmol) in 250 mL acetic acid. To the mixture was added a solution of 19.3 g (232 mmol) 3-aminopyrazole (10) and 270 mL acetic acid. The reaction mixture was stirred at room temperature for 20 h. The product was precipitated by adding 550 mL water. The resulting slurry was aged for 20 h. The solid was filtered, washed with 300 mL water, then dried at 50° C. under <10 mbar for 72 h delivering 74 g of compound 11.

A 1.5 L 4-necked round bottom flask equipped with a thermometer, a mechanical stirrer and an inert gas supply, were charged with 71.3 g (215 mmol) of 11 and 715 mL acetic acid, N-Iodosuccinimide (NIS) 53.52 g (226 mmol, 1.05 eq.) was added in one portion and the yellow suspension was stirred at room temperature for 3 h. The reaction mixture was diluted with 715 mL water to precipitate the product. The slurry was aged for 20 h. The product was filtered, washed with 680 mL water and dried at 50° C. under <10 mbar for 48 h to provide 96.7 g of compound 7.

Example 8

This example illustrates a method for the preparation of compound 3.

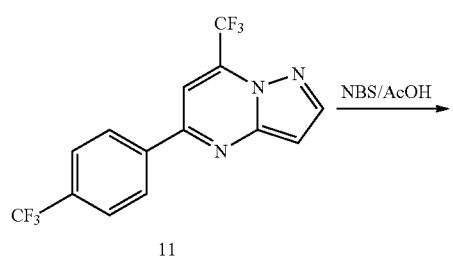

11

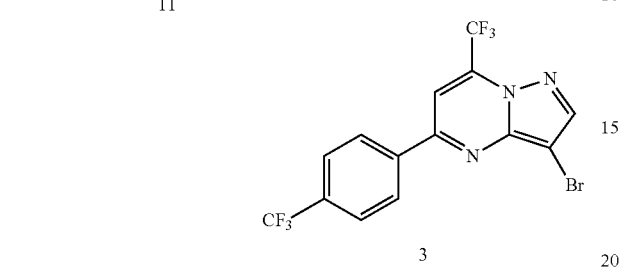

3

To a solution of compound 11 (1.0 g, 3.0 mmol) in AcOH (10 mL) was added N-bromosuccinimide (NBS, 0.58 g, 3.2 mmol). The solution was stirred at RT for 1 h then diluted with water (10 mL). The yellow suspension was cooled to 5° C., stirred for 0.5 h, then filtered. The crystalline product was washed with water (20 mL), then dried for 16 h at 40° C./20 mb to provide compound 3 (1.15 g) with a purity of 100% (HPLC, area-%).

Example 9

This example illustrates a method for the preparation of compound 12.

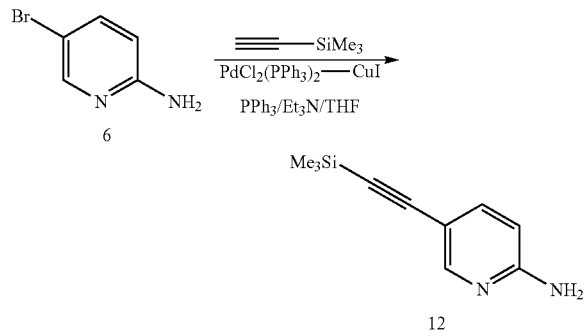

A 2.5 L 4-necked round bottom flask equipped with a thermometer, a mechanical stirrer and an inert gas supply, were charged sequentially 950 mL triethylamine, 100 g (566.4 mmol) 2-amino-5-bromopyridine (compound 6), 8.11 g (11.3 mmol, 0.02 eq.) bis-(triphenylphosphine)-palladium(II)-dichloride, 6.26 g (22.7 mmol, 0.04 eq.) triphenylphosphine, and 2.2 g (11 mmol, 0.02 eq.) copper(I) iodide. To the stirred mixture was added 96.5 g trimethylsilylacetylene (963 mmol, 1.7 eq.). The resulting dark brown suspension was stirred at 75° C. for 17 h. On cooling to room temperature, the reaction mixture was filtered through 40 g Dicalit with the aid of 300 mL triethylamine. The filtrate was evaporated at 50° C. under a reduced pressure of 200 mbar until a volume of ~600 mL then at 200-180 mbar at a constant volume exchange with 850 mL n-heptane. Upon cooling to room temperature, an additional 200 ml n-heptane was added and crystallization was completed at room temperature for 16 h. The product was filtered, washed with 400 mL n-heptane, and dried at 45° C. under <10 mbar for 3 h to afford 90.4 g of crude 12. The crude compound 12 was purified by column chromatography (silica gel), eluting with ethyl acetate and n-heptane (2:1, v/v) to yield 83.4 g of compound 12.

Example 10

This example illustrates a method for the preparation of compound 9.

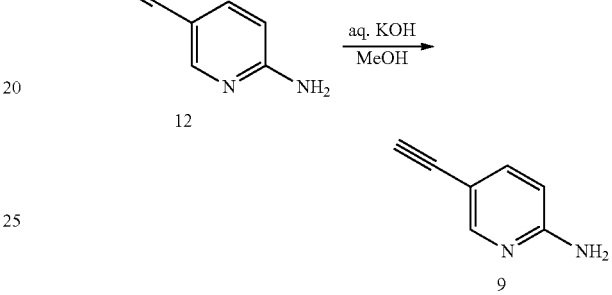

A 1.5 L 4-necked round bottom flask equipped with a thermometer, a mechanical stirrer and an inert gas supply, were charged with 80 g (420.3 mmol) of compound 12, 700 mL ethanol, and a solution of 2.7 g (41.1 mmol, 0.1 eq.) potassium hydroxide in 10 ml water. The mixture was stirred at room temperature for 1 h. The mixture was concentrated at 50° C. under 260-230 mbar to remove ca. 500 solvent. 750 mL. Water were added and the remaining EtOH was evaporated at 60° C. under 65 mbar. The mixture was extracted once with 750 mL, twice with 250 mL, a total of 1250 ethyl acetate. The combined organic phases containing some insoluble material were dried over 80 g sodium sulfate, filtered and the wet cake was rinsed with 50 mL ethyl acetate. The filtrate was evaporated under reduced pressure (240 mbar) at 50° C. to a volume of ~350 mL. A quantity of 700 mL n-Heptane was added with constant volume exchange at 50° C. under 240-210 mbar. An additional 100 ml n-heptane was added and crystallization was completed at room temperature for 1 h. The product was filtered, washed with 350 ml n-heptane and dried at room temperature under <10 Mbar for 3 h to provide 49 g of compound 9.

Example 11

This example illustrates a method for the preparation of compound 9.

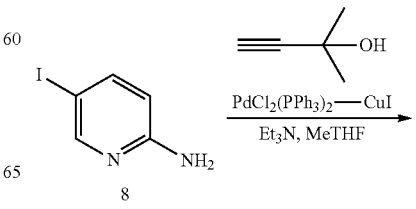

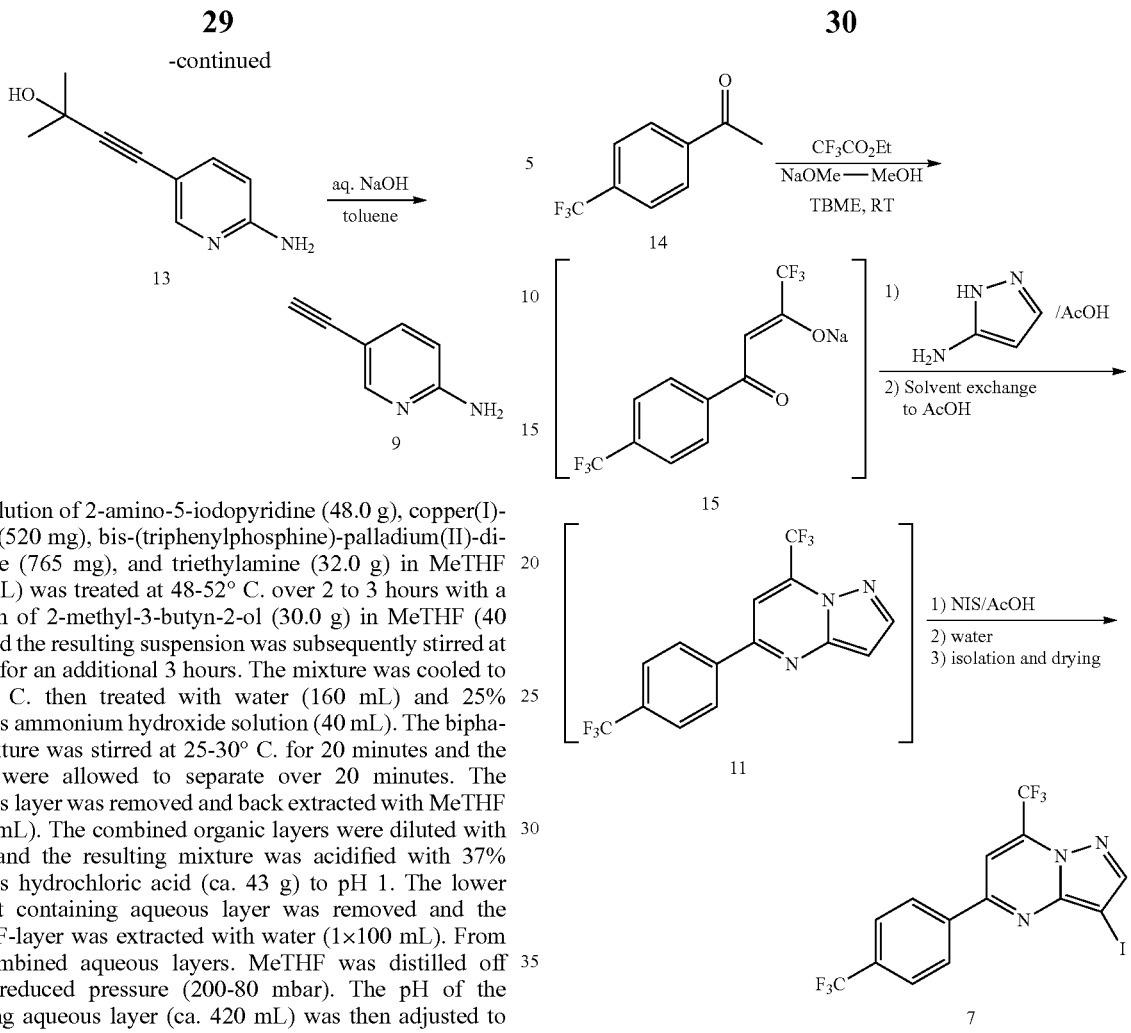

A solution of 2-amino-5-iodopyridine (48.0 g), copper(I)-iodide (520 mg), bis-(triphenylphosphine)-palladium(II)-dichloride (765 mg), and triethylamine (32.0 g) in MeTHF (220 mL) was treated at 48-52° C. over 2 to 3 hours with a solution of 2-methyl-3-butyn-2-ol (30.0 g) in MeTHF (40 mL) and the resulting suspension was subsequently stirred at 50° C. for an additional 3 hours. The mixture was cooled to 25-30° C. then treated with water (160 mL) and 25% aqueous ammonium hydroxide solution (40 mL). The biphasic mixture was stirred at 25-30° C. for 20 minutes and the layers were allowed to separate over 20 minutes. The aqueous layer was removed and back extracted with MeTHF (2×80 mL). The combined organic layers were diluted with water and the resulting mixture was acidified with 37% aqueous hydrochloric acid (ca. 43 g) to pH 1. The lower product containing aqueous layer was removed and the MeTHF-layer was extracted with water (1×100 mL). From the combined aqueous layers. MeTHF was distilled off under reduced pressure (200-80 mbar). The pH of the resulting aqueous layer (ca. 420 mL) was then adjusted to pH 9-10 by addition of 28% aqueous sodium hydroxide solution (ca. 37 g) at 15-20° C. At pH 5 the product started to precipitate. The resulting suspension was stirred for 2 hours at 15 to 20° C. and the product was filtered and washed in two portions with water (300 mL in total). The wet crystalline mass (ca. 46 g) was dried at 40° C. and <30 mbar until constant weight affording 33.56 g (87% yield) of compound 13, as yellow-beige crystals with a purity of 99.5% (HPLC, area-%).

A suspension of compound 13 (17.10 g) and sodium hydroxide (12.2 g) toluene (170 mL) was heated under reduced pressure (approx. 750 Mbar) to 95 to 102° C. within 30 to 60 minutes (approx. 110° C. jacket temperature). The mixture was subsequently stirred at this temperature for 4 to 7 hours. Upon complete conversion (<2% starting material), the mixture was cooled to 80-86° C. and washed at this temperature three times with water (45 mL and 2×30 mL). The combined aqueous layers were back extracted at room temperature with MeTHF (80 mL). The combined toluene and MeTHF layers were concentrated to almost dryness. The residue was dissolved in 120 mL of MeTHF and subsequently polish filtered. The filter cake was rinsed with MeTHF (2×25 mL) furnishing 157.16 g solution of compound 9 with an assay of 6.4% (w/w), corresponding to a corrected yield of 88%.

Example 12

This example illustrates a "one-pot" method for the preparation of compound 7.

To a dry, clean, 2.50 mL Erlenmeyer flask was added 45.32 g of 4'-trifluoromethylacetophenone (14) and 94.8 g of tert-butyl methyl ether (MTBE). The resulting mixture was stirred at 20° C. under nitrogen for 10-20 min. to provide a clear solution. The solution was transferred to a 250 mL addition funnel.

To a dry, clean, 500 mL round bottom flask was added 70.0 g of 25 wt % methanol solution of sodium methoxide and 39.52 g of ethyl trifluoroacetate. The resulting mixture was stirred under nitrogen and cooled to 20° C. The 4'-trifluoromethylacetophenone solution was added in 15-30 min. The 250 mL Erlenmeyer flask was rinsed with 7.4 g of MTBE and the rinse was added to the batch via the same addition funnel. The resulting mixture was stirred under nitrogen at 20±5° C. for 3-4 hr to complete the conversion from 14 to 15. This solution was added to a 1000 mL 3-neck round bottom flask containing 336 g of glacial acetic acid and 19.42 g of 3-aminopyrozale. The resulting mixture was stirred at 40-50° C. under nitrogen for 2 hr to complete the conversion from 15 to 11. The batch was heated to distill out ~344 g solvent under atmospheric pressure (final pot temperature ca. 115° C.). To the batch was added 105 g of glacial acetic acid and the atmospheric distillation was continued until ~105 g solvent was collected (final pot temperature ca. 123° C.). The mixture was cooled to 40±5° C. providing a solution of crude 11 in acetic acid.

To a 2000 mL 4-neck jacketed round bottom flask, equipped with an overhead agitator, thermal couple and funnel, was added 62.3 g of NIS and 336 g of glacial acetic acid. The resulting mixture was stirred at 40° C. while the crude 11 solution was added. Stirring was continued at 40±5° C. for 3-4 hr. The batch temperature was then raised to 65±5° C. and 750 g of an aqueous solution of sodium thiosulfate (13.7 g in 740 mL water) was added. The reaction mixture was stirred at 65±5° C. for 1 h, cooled to 20° C., and aged for 2 hr. The solid was filtered through a 600 mL coarse filtration funnel. The wet cake was washed with 700 g of water, dried at 65±5° C. under vacuum for ≥15 hr affording 104 g of compound 7 as a bright yellow solid.

Example 13

This example illustrates another "one-pot" method for the preparation of compound 7.

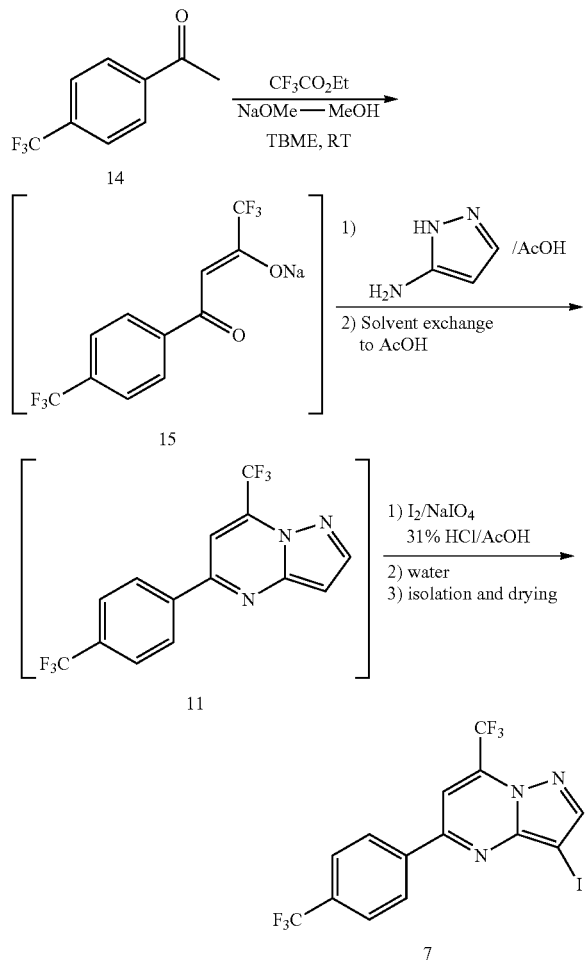

The 250 mL Erlenmeyer flask was rinsed with 7.4 g of MTBE, and the rinse was added to the batch via the same addition funnel. The resulting mixture was stirred under nitrogen at 20±5° C. for 3-4 hr to complete the conversion from 14 to 15. This solution was added to a 1000 mL 3-neck round bottom flask containing 315 g of glacial acetic acid. To the mixture was added a solution of 19.42 g of 3-aminopyrozale in 49 g of methanol. The resulting mixture was stirred at 40-50° C. under nitrogen for 2 hr to complete the conversion from 15 to 11. The batch was heated to distill out ~316 g solvent under atmospheric pressure (final pot temperature ca. 115° C.). To the batch was added 189 g of glacial acetic acid and the atmospheric distillation was continued until 165 g solvent was collected (final pot temperature 126° C.). The batch was cooled to 40±5 C. providing a solution of crude 11 in acetic acid.

To a 2000 mL 4-neck jacketed round bottom flask, equipped with an overhead agitator, thermal couple and funnel, was added 33.6 g of iodine, 8.82 g of sodium periodate and 168 g of glacial acetic acid. The resulting mixture was stirred at 40° C. while the crude 11 solution was added. Over 15 min, 47.5 g of 31% aqueous hydrochloric acid was added via an additional funnel while maintaining batch temperature at 40±5° C. The reaction mixture was stirred at 40±5° C. for 1 h. The batch temperature was then raised to 65±5° C. and agitation was continued for another hour to complete the reaction. The reaction mixture was cooled to 40° C. and over a period of 30-60 min, 180 g of water was added at 40±5° C. After further cooling over 1 h to 20° C., 375 g of an aqueous solution of sodium thiosulfate (15.1 g in 360 mL water) was added at 20° C. over a period of 30-60 min. The batch was stirred for 2 hr at 20° C. then filtered through a 600 mL coarse filtration funnel. The wet cake was washed with 360 g of water, dried at 65±5° C. under house vacuum for ≥15 hr and afforded 105 g of compound 7 as a bright yellow solid.

Example 14

This example illustrates a method for the preparation of crude compound A.

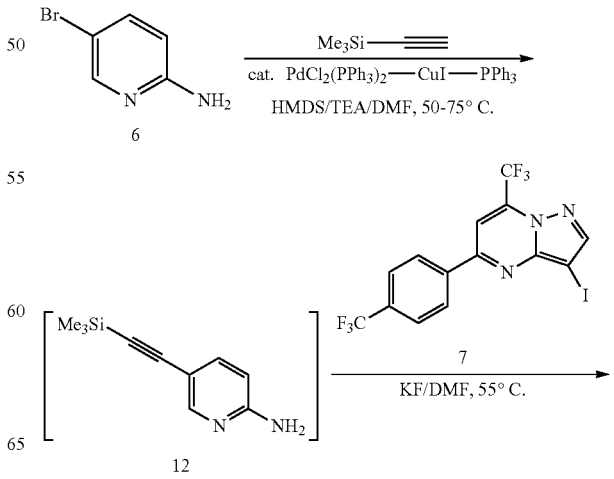

To a dry, clean, 250 mL Erlenmeyer flask is added 45.32 g of 4'-trifluoromethylacetophenone (14) and 94.8 g of tert-butyl methyl ether (MTBE). The resulting mixture was stirred at 20° C. under nitrogen for 10-20 min. furnishing a clear solution. The solution was transferred to a 250 mL addition funnel.

To a dry, clean, 500 mL round bottom flask was added 70.0 g of 25 wt % methanol solution of sodium methoxide and 39.52 g of ethyl trifluoroacetate. The resulting mixture was stirred under nitrogen and cooled to 20° C. The 4'-trifluoromethylacetophenone solution was added in 15-30 min.

-continued

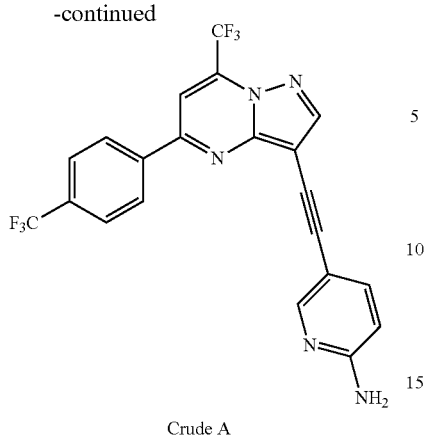

Crude A

A 300 mL resin flask, equipped with a chiller, mechanical stirrer, reflux condenser, argon inlet, thermocouple and septum was charged with 34.06 g of 2-amino-5-bromopyridine (1.2 eq.), 2.76 g of (PPh$_3$)$_2$PdCl$_2$ (2.4 mol %), 2.06 g of PPh$_3$ (4.8 mol %), 0.75 g of CuI (2.4 mol %), and 257 g of TEA (triethylamine) (15.5 eq.). The mixture was stirred at 20° C. giving a yellow slurry then heated to 75° C. To this mixture was added portionwise 21.3 g of TMS-acetylene (1.32 eq.). The total charge was divided into 4 approximately equal portions which were added at t=0, 2, 4, and 6 hours. The hatch was held at 75° C. for 9-17 hours after the TMS-acetylene addition was complete (15-22 hours total). The batch was cooled to 30° C. A vacuum distillation to approximately minimum stirring volume was performed (distillation end point: jacket <50° C., Batch ~30° C., 100 mbar). The jacket was set to cool to 20° C. and 177 g of DMF was added. The hatch was pressure-filtered through a celite impregnated disk and the flask and cake were rinsed with 71 g of DMF providing a solution of crude 12.

A 500 mL jacketed reactor equipped with a mechanical stirrer, thermocouple, argon inlet and stopper was charged with 75.0 g of 7 (1.0 eq., limiting reagent), 12.6 g of potassium fluoride (1.32 eq.), 1.66 g of TEA (10 mol %), and 107 g of DMF. The mixture was agitated to give a thick yellow to green slurry. To this mixture was added all of the 12 solution. The batch was heated to 40° C., with a ramp of 1° C./min then heated further to 55° C. with a ramp of 0.25° C./min. The batch was held at 55° C. for 2 h. The batch was cooled to 20° C. and added slowly to 1240 g of water at 15±5° C. giving a rusty orange colored slurry. The resulting mixture was agitated and held for 2 hours at 15° C. generating a deep blood red colored slurry. The solid was filtered. The reactor and wet cake were rinsed with 450 g of water. The cake was dried at 50° C. under vacuum with an air bleed overnight giving the crude compound A as a dark red, slightly clumpy powder.

Example 15

This example illustrates another method for the preparation of crude compound A.

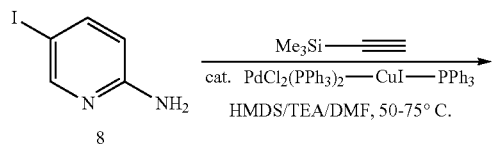

-continued

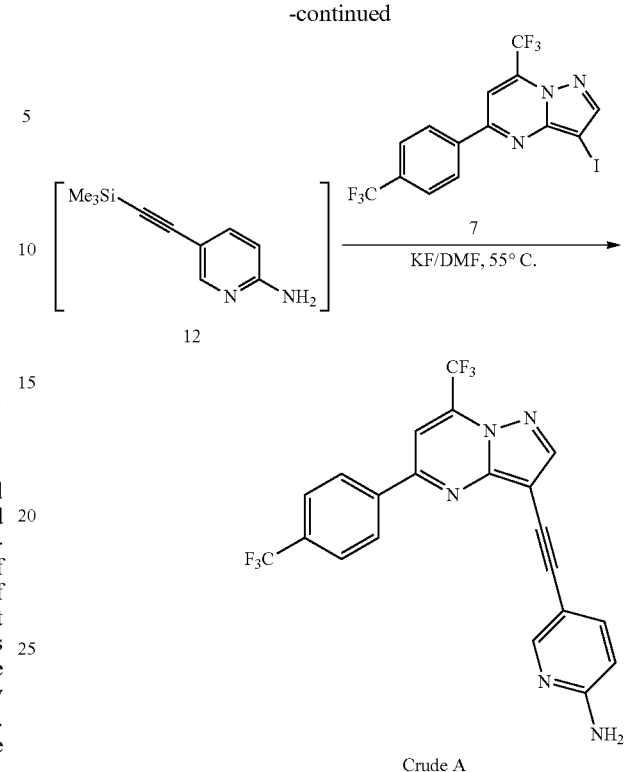

A 300 mL resin flask, equipped with a chiller, mechanical stirrer, reflux condenser, argon inlet, thermocouple and septum was charged with 11.1 g of 2-amino-5-iodopyridine (1.15 eq.), 0.737 g of (PPh$_3$)$_2$PdCl$_2$ (2.4 mol %), 0.551 g of PPh$_3$ (4.8 mol %), 0.20 g of CuI (2.4 mol %), and 94.4 g of DMF (N,N-dimethylformamide). The mixture was stirred at 20° C. giving a thin amber suspension. To this mixture was charged of 1,1,1,3,3,3-hexamethyldisilazane (0.24 eq.). To the resulting dark amber solution was added 13.3 g of TEA (triethylamine) (3.0 eq.). The reaction mixture was heated to 50° C. and 4.94 g of TMS-acetylene (1.15 eq.) was added portionwise. The total charge was divided into 2 approximately equal portions which were added at t=0 and 1 hour. The batch was held at 50° C. for 3 hours after the TMS-acetylene addition was complete (4 hours total) then cooled to 20° C. providing a solution of crude 12.

To the batch was charged 20.0 g of 7 (1.0 eq.) and 4.32 g of potassium fluoride (1.70 eq.). The solids that remained in the funnel were rinsed in with DMF (~5 mL). The batch was heated to 40° C. with a ramp of 1° C./min and then heated further to 55° C. with a ramp of 0.25° C./min. The reaction mixture was held at 55° C. for 2 hours, cooled to 20° C. then added slowly to 330 g of water over ~30 minutes while maintaining the batch temperature at 15±5° C. A rusty orange colored slurry formed which darkened to a deep blood red color. The batch was agitated, held for 2 hours at 15° C. then filtered. The reactor and wet cake were rinsed with 120 g of water. The cake was dried at 50° C. under vacuum with an air bleed overnight providing 21.7 g of crude compound A as a dark red, free-flowing powder.

Example 16

This example illustrates a method for the preparation of pure compound A.

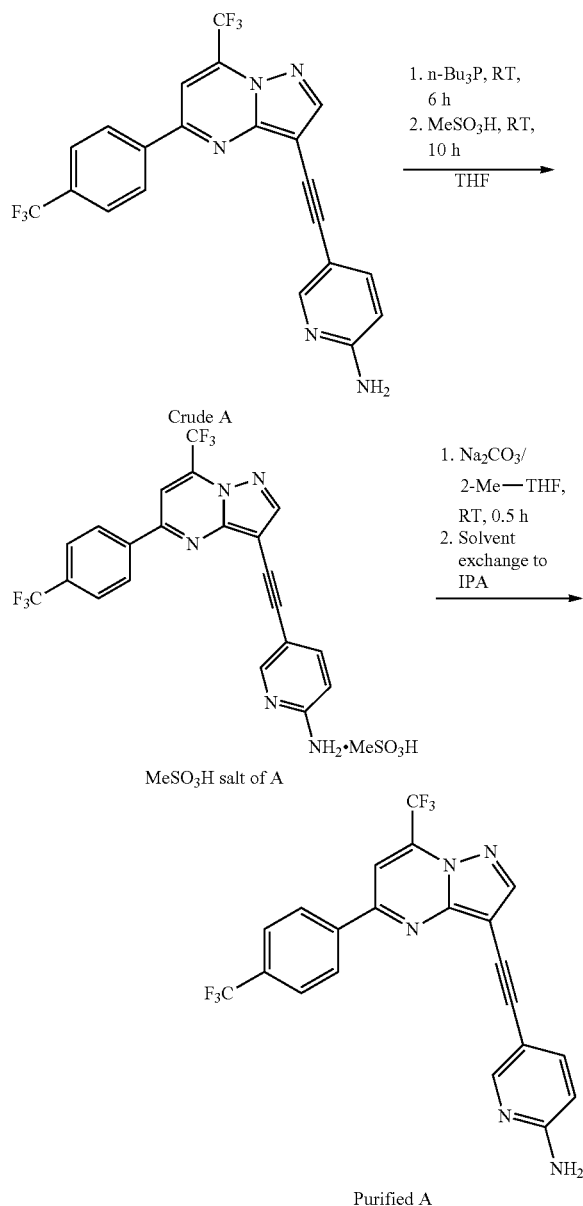

A 500 mL four-neck jacketed reactor (Reactor 1), equipped with overhead stirrer, temperature probe, reflux condenser and nitrogen inlet was charged with 35.78 g of crude compound A (80 mmol, 1.0 eq.) and 160 mL, (140.8 g) of THF. Agitation was started giving a dark brown solution and 20 mL (16.2 g) of n-tributylphosphine (80 mmol, 1.0 eq.) was added via a syringe over ~5 minutes at room temperature. The mixture was stirred for 6 hours at room temperature then 8 mL (11.8 g) of methanesulfonic acid (120 mmol, 1.5 eq.) was added dropwise over ~5 minutes. The yellow-brown slurry was stirred at room temperature for 10 hours, filtered through a 350 mL fine glass filter and the yellow wet cake was washed with 2×30 mL (26.4 g) of THF. The methanesulfonic salt was dried at 40° C. under full vacuum overnight (28.19 g obtained).

The dry salt was charged to a 500-mL reactor (Reactor 2) and 220 mL (189.2 g) of 2-Me THF was added. Agitation was started giving a yellow slurry. In an Erlenmeyer flask, 12.71 g of sodium carbonate (120 mmol, 1.5 eq.) was dissolved in 140 mL (140 g) of DI water and this basic solution was added dropwise to the yellow slurry. The solids dissolved during the course of the addition giving a dark brown solution (pH check: >9). The biphasic solution was stirred at room temperature for ~30 minutes and the batch was filtered over a celite impregnated disc. The flask and the celite bed were rinsed with 2×30 mL (25.8 g) of 2-Me THF. The filtrate and the rinse were transferred back to the reactor and layers were allowed to separate. The lower aqueous layer was drained and the top organic layer was washed with 140 mL (140 g) of deionized (DI) water. The organic layer was charged back to a clean 500 mL reactor (Reactor 3) and the solvent was distilled under reduced pressure (620 mbar, jacket temperature: 70° C.) until ~100 mL (~80 g) distillate was collected. The vacuum was released and 100 mL (78.5 g) of 2-propanol was added dropwise to the batch over ~15 minutes. Distillation under reduced pressure (530 mbar, jacket temperature: 70° C.) was continued until 190 mL (~160 g) of distillate was collected. The vacuum was released again and 160 mL (125.6 g) of 2-propanol was added dropwise over ~15 minutes. Further distillation under reduced pressure (400 mbar, jacket temperature: 70° C.) removed a further ~160 mL (~130 g) of distillate. The vacuum was released a final time and 160 mL (125.6 g) of 2-propanol was added dropwise to the batch over ~15 minutes. The mixture was heated to ~80° C., stirred for 2 hours then cooled to 20° C. The bright orange slurry was stirred at this temperature for 10 hours and the product was filtered on a 350 mL fine glass filter. The wet cake was washed with 2×30 mL (23.6 g) of 2-propanol and the product was dried at 50° C. under full vacuum overnight rendering 21.8 g of purified compound A.

Example 17

This example illustrates a method for the preparation of compound 13 from compound 6.

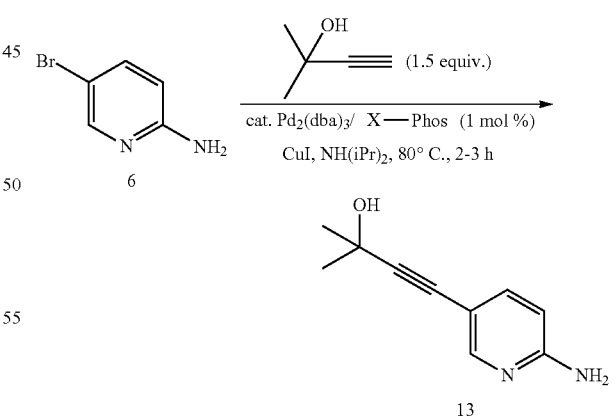

A 100 ml 4-necked flask was charged with 5-bromo-2-aminopyridine (5 g, 28.9 mmol) and diisopropylamine (61.8 ml, 433 mmol, 15 equiv.). The mixture was degassed upon argon introduction while tris(dibenzylideneacetobe)dipalladium(0) (132 mg, 144 µmol, 1 mol % Pd), X-Phos (165 mg, 347 µmol, 1.2 mol %), copper iodide (110 mg, 578 µmol, 2 mol %) and 2-methyl-3-butyn2-ol (3.65 g, 43.3 mmol, 1.5 equiv.) was added successively. The reaction mixture was heated to 80° C. and stirred at this temperature for 2 h. Then the heating was stopped and the black suspension was cooled in a water bath to ambient temperature. To this suspension were added 2-Me-THF (30 ml) and water (20 ml). The phases were separated, the aqueous phase was washed with 2-Me-THF (50 ml) and the organic phase was washed with water (50 ml). From the combined organic phases the solvent was removed under vacuum to dryness. The dark residue was suspended in water (30 ml), HCl (4 ml, 25%) was added (~pH 1) and the mixture was stirred for 30 min. The dark insoluble residues were filtered off and the yellow solution was treated with NaOH (4 ml, 32%, pH 10) whereupon crystallization was initiated. The suspension was stirred for 30 min., the crystals were filtered off, washed with water and dried under vacuum to weight constancy to yield compound 13 as yellow crystals (4.8 g, 93% yield, 98.5% area %, HPLC).

Example 18

This example illustrates another method for the preparation of compound 1 from compound 6.

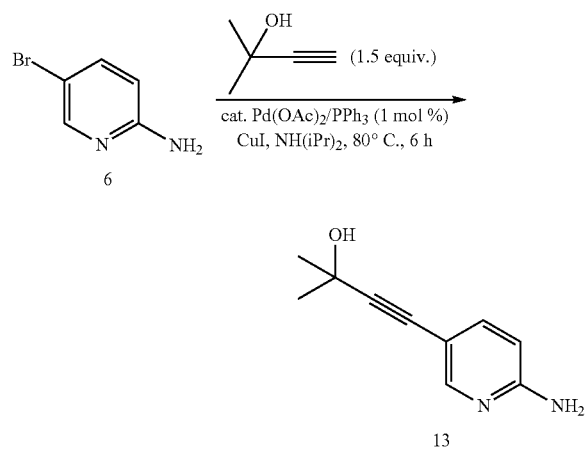

A 100 ml 4-necked flask was charged with 5-bromo-2-aminopyridine (5 g, 28.9 mmol) and diisopropylamine (61.8 ml, 433 mmol, 15 equiv.). The mixture was degassed upon argon introduction while adding palladium(II) acetate (64.9 mg, 289 µmol, 1 mol %), triphenylphosphine (303 mg, 1.16 mmol, 4 mol %) and copper iodide (110 mg, 578 µmol, 2 mol %), and the reaction mixture was heated to 80° C. At this temperature 2-methyl-3-butyn2-ol (3.65 g, 43.3 mmol, 1.5 equiv.) was added over a period of 15 min., and the reaction mixture was stirred at this temperature for 17 h. Then the heating was stopped and the black suspension was cooled in a water bath to ambient temperature. To this suspension was added 2-Me-THE (30 ml) and water (20 ml). The phases were separated, the aqueous phase was washed with 2-Me-THF (30 ml), and the organic phase was washed with brine (30 ml). From the combined organic phases the solvent was removed under vacuum to dryness. The dark residue was suspended in HCl (20 ml, aq, 2M) to adjust the pH to pH 1, and the mixture was stirred for 10 min. The dark insoluble residues were filtered off and the yellow solution was treated with NH₃ (aq., 25%, 4 ml, pH 8.5-9) whereupon crystallization was initiated. The suspension was stirred for 20 min., the crystals were filtered off, washed with water (8 ml) and dried under vacuum to weight constancy to yield compound 13 as beige crystals (4.7 g, 92% yield, 99.2. area %, HPLC).

Example 19

This example illustrates another method for the preparation of compound 13 from compound 6.

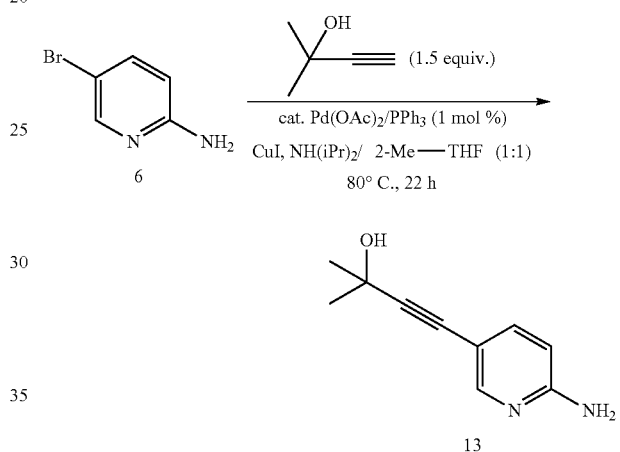

A 650 ml 4-necked flask was charged with 5-promo-2-aminopyridine (30 g, 173.4 mmol), diisopropylamine (185 ml, 1.3 mol, 7.5 equiv.) and 2-Me-THF (180 ml). The mixture was degassed upon argon introduction while adding palladium(II) acetate (389 mg, 1.73 mmol, 1 mol % Pd), triphenylphosphine (1.82 g, 6.94 mmol, 4 mol %) and copper iodide (660 mg, 3.47 mmol, 2 mol %) successively and the reaction mixture was heated to 80° C. At this temperature was added over a period of 30 min 2-methyl-3-butyn2-ol (21.9 g, 260 mmol, 1.5 equiv.) and the reaction mixture was stirred at 80° C. for additional 21.5 h. Then the heating was stopped and the black suspension was cooled in a water bath to ambient temperature. To the dark suspension was added water (100 ml) and 2-Me-THF (100 ml) and the mixture was filtered over dicalite. Afterwards, the phases were separated, the organic phase was washed with brine (200 ml), whereas the water phase was washed with 2-Me-THF (250 ml). From the combined organic phases the solvent was removed under vacuum to give a brown solid, which was suspended in water (200 ml). This suspension was treated with HCl (25%, 24 ml, pH 1) and the mixture was stirred for 10 min. The black precipitate was removed by filtration and the mother liquor was treated with heptane (100 ml). Afterwards, the phases were separated, the aqueous phase was treated with NH₃ (aq., 25%, 30 ml) and the

39 pH was adjusted to pH 10, whereupon the product precipitated. The suspension was stirred for 30 min, the crystals were filtered off, washed successively with water (50 ml) and heptane (10 ml) and dried under vacuum to weight constancy to yield compound 13 as a yellow solid (26.5 g, 85% yield, 98 area % HPLC).

Example 20

This example illustrates a method for the preparation of compound 13 from compound 8.

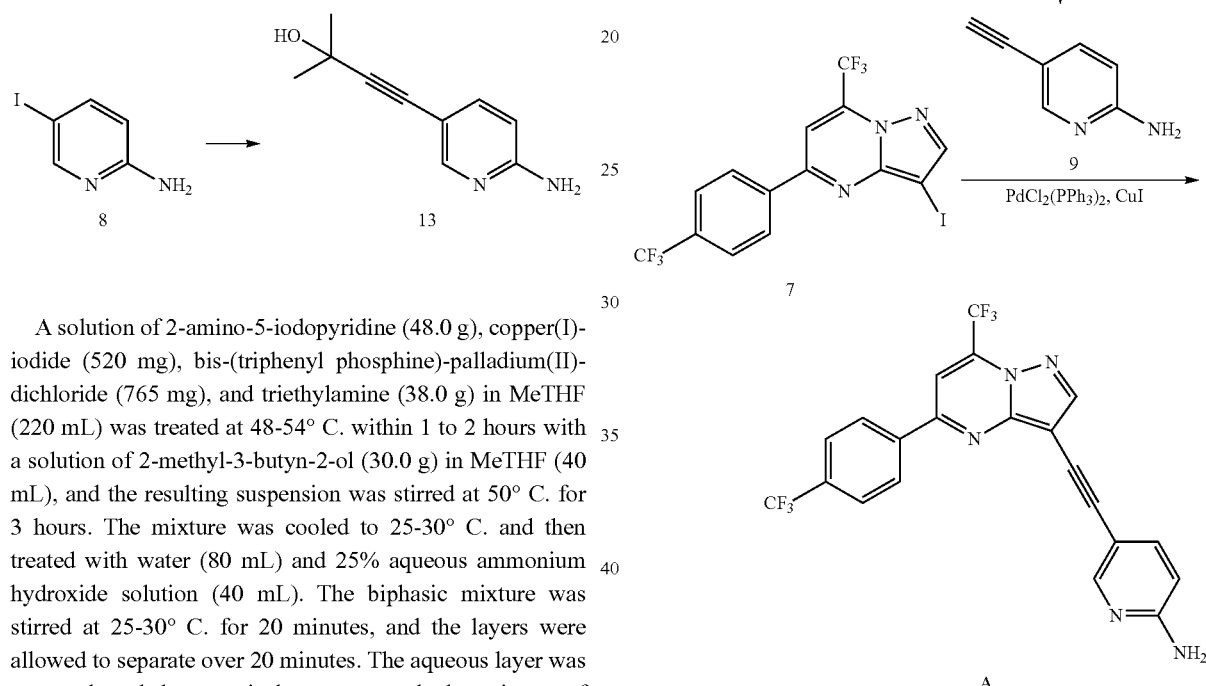

A solution of 2-amino-5-iodopyridine (48.0 g), copper(I)-iodide (520 mg), bis-(triphenyl phosphine)-palladium(II)-dichloride (765 mg), and triethylamine (38.0 g) in MeTHF (220 mL) was treated at 48-54° C. within 1 to 2 hours with a solution of 2-methyl-3-butyn-2-ol (30.0 g) in MeTHF (40 mL), and the resulting suspension was stirred at 50° C. for 3 hours. The mixture was cooled to 25-30° C. and then treated with water (80 mL) and 25% aqueous ammonium hydroxide solution (40 mL). The biphasic mixture was stirred at 25-30° C. for 20 minutes, and the layers were allowed to separate over 20 minutes. The aqueous layer was removed, and the organic layer was washed a mixture of water (40 mL) and 25% aqueous ammonium hydroxide solution (40 mL). The combined aqueous layers were back extracted with MeTHF (100 mL). The combined organic layers were washed with water (30 mL) and then concentrated under reduced pressure to a residual volume of approx, 80 mL. Toluene (500 mL) vas then added, and the mixture was concentrated under reduced pressure to a residual volume of approx. 400 mL. The mixture was treated with isopropanol (60 mL) and tributyl phosphine (2 mL). The suspension was heated to reflux temperature to obtain a clear solution and subsequently cooled 0° C. within 5 h whereby the product crystallized. The resulting suspension was stirred at 0° C. for four hours. The product was filtered and washed with 80 mL of toluene. The wet crystals were dried at 50° C. and <30 mbar until constant weight affording 32.8 g (85% yield) of compound 13 as slightly yellow crystals with a purity of 99.9% (HPLC, area-%) and an assay of 100.0% (HPLC, w/w-%).

40

Example 21

This example illustrates a method for the preparation of compound A from compound 13.

A suspension of compound 13 (17.6 g), sodium carbonate (23.0 g) and sodium hydroxide (3.0 g) in toluene (200 mL) was heated under reduced pressure (approx. 800 mbar) to 100 to 105° C. and subsequently stirred at this temperature for 6 to 10 hours. During the reaction, distilled toluene is continuously replaced with fresh toluene keeping the volume constant. Upon complete conversion (<2% of starting material), the mixture was cooled to 50° C. and half of the toluene was distilled off under reduced pressure. MeTHF (120 mL) and water (120 mL) were added and the biphasic mixture was stirred for 30 minutes. The layers were allowed to separate and the lower aqueous layer subsequently removed. The organic layer was polish filtered; the filtrate washed with water (1×40 mL) and subsequently concentrated to dryness. The residue was dissolved in 150 of MeTHF. This solution was subsequently added within 2 to 3 hours to a hot (70-75° C.) solution of compound 7 (36.0 g), copper(I) iodide (334 mg), bis-(triphenylphosphine)-palladium(II)-dichloride (557 mg), triphenyl phosphine (414 mg) and triethylamine (25.5 mL) in MeTHF (145 mL) and the resulting suspension was stirred at 70-75° C. for additional 14 hours. The mixture was cooled to 30° C. and treated with water (150 mL) and 25% aqueous ammonium hydroxide solution (30 mL). The biphasic mixture was stirred for 30 minutes and the layers were then allowed to separate for 20 minutes. The aqueous layer was removed and the MeTHF layer was washed twice with a mixture of water (150 mL) and 25% aqueous ammonium hydroxide solution (30 mL). The MeTHF layer was subsequently washed with water (3×150 mL). The organic layer was polish filtered, and the filtrate was treated with n-tributylphosphine (1.0 mL). MeTHF was completely distilled off and replaced by ethanol (500 mL in total) at atmospheric pressure. The resulting suspension (approx. 300 mL) was heated to reflux and stirred at reflux for 2 hours and then cooled to room temperature overnight. The product was filtered and washed with ethanol (50 mL). The wet crystals were dried at 50° C. and <30 mbar until constant weight affording 29.3 g (83% yield based on 7) of compound A as red crystals with a purity of 99.5% (HPLC, area-%) and an assay of 99.0% (HPLC, w/w-%).

The crystallization in above example can also be done with isopropanol instead of ethanol. The product may be further purified by reprocessing (recrystallization by dissolving the product in MeTHF followed by solvent exchange to isopropanol or ethanol and subsequent isolation).

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

The invention claimed is:
1. A method for preparing compound 9 having the formula:

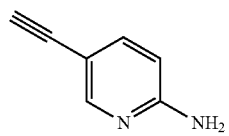

9 which comprises:
(a) reacting compound 8;

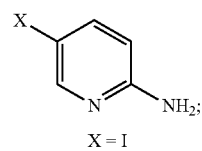

8

X = I with 2-methyl-3-butyn-2-ol via a Sonogashira coupling reaction in an inert solvent to provide compound 13; and

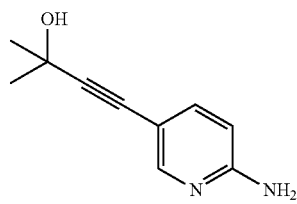

13 b) deprotecting compound 13 with a base in an inert solvent to provide compound 9.

* * * * *